United States Patent [19]

Adams et al.

[11] Patent Number: 5,516,052

[45] Date of Patent: May 14, 1996

[54] MEDICAL WASTE COLLECTION AND TREATMENT SYSTEM

[75] Inventors: Mathew J. Adams; Kenneth R. Lamaster, both of Indianapolis; David B. Mennel; Jeffrey C. Rapp, both of Greenwood; Joseph H. Wilson, Speedway, all of Ind.

[73] Assignee: Ecomed, Inc., Indianapolis, Ind.

[21] Appl. No.: 208,989

[22] Filed: Mar. 9, 1994

Related U.S. Application Data

[63] Continuation-in-part of Ser. No. 73,758, Jun. 8, 1993, Pat. No. 5,465,841, which is a continuation-in-part of Ser. No. 882,915, May 19, 1992, Pat. No. 5,236,135, which is a continuation-in-part of Ser. No. 704,455, May 23, 1991, Pat. No. 5,240,187.

[51] Int. Cl.$^6$ .............................. B02C 13/16; B02C 13/26
[52] U.S. Cl. ................ 241/189.1; 241/194; 241/199.12; 241/606
[58] Field of Search .................. 241/99, 606, 199.12, 241/194, 189.1, 242, 282.1, 282.2, 285.1; 366/314

[56] References Cited

U.S. PATENT DOCUMENTS

| | | | |
|---|---|---|---|
| 1,592,601 | 7/1926 | Hines. | |
| 2,635,784 | 4/1953 | Bering et al. | 220/44 |
| 2,656,985 | 10/1953 | Backlund et al. | 241/194 X |
| 2,660,210 | 11/1953 | Berglind | 146/68 |
| 2,820,595 | 1/1958 | Schumacher | 241/99 |
| 2,912,176 | 11/1959 | Jordan | 241/194 |
| 3,049,306 | 8/1962 | Nowlin | 241/194 X |
| 3,156,278 | 11/1964 | Otto | 146/67 |
| 3,181,802 | 5/1965 | Lung et al. | 241/194 X |
| 3,186,652 | 6/1965 | Hardy et al. | 241/194 X |
| 3,211,389 | 10/1965 | Sherman, Jr. | 241/194 X |
| 3,389,864 | 6/1968 | Topinka | 241/141 |
| 3,403,865 | 10/1968 | Guth et al. | 241/194 X |
| 3,434,518 | 3/1969 | Motis | 146/68 |
| 3,436,029 | 4/1969 | Lopp et al. | 241/194 |
| 3,528,469 | 9/1970 | Mantelet | 146/68 |
| 3,596,692 | 8/1971 | Swanke | 146/68 |
| 3,814,332 | 6/1974 | Nakao | 241/38 |
| 3,901,349 | 8/1975 | DeNoyer | 181/33 |
| 4,194,697 | 3/1980 | Lembeck | 241/92 |
| 4,269,364 | 5/1981 | Moriconi et al. | 241/36 |
| 4,275,848 | 6/1981 | Webb, Sr. | 241/46 |
| 4,578,185 | 3/1986 | Wilson et al. | 210/85 |
| 4,586,666 | 5/1986 | Fox | 241/282.2 |
| 4,609,156 | 9/1986 | Boele | 241/199.12 |
| 4,618,103 | 10/1986 | Wilson et al. | 241/41 |
| 4,619,409 | 10/1986 | Harper et al. | 241/38 |

(List continued on next page.)

FOREIGN PATENT DOCUMENTS

| | | |
|---|---|---|
| 1394972 | 2/1964 | France. |
| 61-25432 | 2/1986 | Japan. |
| 725700 | 4/1980 | U.S.S.R.. |
| 1142167 | 2/1985 | U.S.S.R.. |
| 1546076A1 | 2/1990 | U.S.S.R. ................. 42/26 |

*Primary Examiner*—Timothy V. Eley
*Attorney, Agent, or Firm*—Willian Brinks Hofer Gilson & Lione

[57] ABSTRACT

An apparatus for the treatment of medical waste, including solid and non-solid materials, permits the collection of such medical waste at the point and at the time of its generation in a solid container. The contained medical waste can be subsequently transported for pulverization, decontamination and safe disposal. A separate portable processing chamber, with an integral means to treat medical waste, can be used at locations remote from its power unit for the collection of medical waste and then moved to the location of the power unit to drive the waste-treatment means within the chamber. The separate portable processing chamber includes a rotating waste treatment system that is rotatably carried within the chamber, a plurality of pivotable blades that are carried by rotatable axle pins within a plurality of slots formed in the rotating system, a ring carried by the rotating system to prevent deleterious collections of waste materials, and a plurality of baffle bars are located interiorly of the chamber for preferential treatment of soft and non-soft medical waste material during operation.

28 Claims, 13 Drawing Sheets

U.S. PATENT DOCUMENTS

| | | | |
|---|---|---|---|
| 4,637,561 | 1/1987 | Edberg | 241/154 |
| 4,809,915 | 3/1989 | Koffsky et al. | 241/36 |
| 4,816,307 | 3/1989 | Honeycutt | 428/34.1 |
| 4,852,814 | 8/1989 | Amiot et al. | 241/37.5 |
| 4,860,961 | 8/1989 | Hilgarth | 241/92 |
| 4,878,627 | 11/1989 | Otto | 241/199.12 |
| 4,884,756 | 12/1989 | Pearson | 241/42 |
| 4,889,290 | 12/1989 | Koffsky et al. | 241/36 |
| 4,955,548 | 9/1990 | Rahill | 241/30 |
| 4,971,261 | 11/1990 | Solomons | 241/99 |
| 4,973,005 | 11/1990 | Hasebrouck et al. | 241/194 |
| 4,984,747 | 1/1991 | Lechner | 241/55 |
| 4,984,748 | 1/1991 | Kimura | 241/65 |
| 5,018,675 | 5/1991 | Gateaud | 241/282.2 |
| 5,054,696 | 10/1991 | Mennel et al. | 241/34 |
| 5,236,135 | 8/1993 | Wilson et al. | 241/21 |
| 5,240,187 | 8/1993 | Wilson | 241/99 |

MEDICAL WASTE COLLECTION AND TREATMENT SYSTEM

This is a continuation-in-part of U.S. patent application Ser. No. 08/073,758, filed Jun. 1993, now U.S. Pat. No. 5,465,841 which in turn is a continuation-in-part of U.S. Ser. No. 07/882,915 filed May 19, 1992, now U.S. Pat. No. 5,236,135, which in turn is a continuation-in-part of U.S. Ser. No. 07/704,455 filed May 23, 1991, now U.S. Pat. No. 5,240,187.

FIELD OF THE INVENTION

This invention relates generally to methods and apparatus for handling and treating medical waste materials, and more particularly to methods and apparatus for decontaminating and rendering infectious solid and soft medical waste items handleable.

DESCRIPTION OF THE PRIOR ART

The treatment of medical waste with one machine is disclosed in U.S. Pat. No. 4,619,409, issued Oct. 28, 1986. It is a comparatively large stationary machine for disintegration and decontamination of hospital waste materials in relatively large volumes. Other patents also disclose medical waste treatment apparatus for hospital use, including U.S. Pat. Nos. 4,578,185; 4,618,103; and 5,054,696. There are many facilities, however, such as medical and dental offices and clinics that do not have such volumes of waste materials, space for such a large machine, or funds to buy such large and expensive machines. One effort to deal with the waste materials of such facilities is presented in U.S. Pat. No. 4,971,261 issued Nov. 20, 1990 to Solomons. That patent discloses a device that is intended to be a portable desktop device. It has a cylindrical body 11, a cover 12, a one-way feed opening 13 in the cover 12, a motor driven rotating blade 20 in the body to fragment the waste, a sweeper blade agitation member 21 rotated by the blade drive motor, and a cut-out 12C of the cover 12 that can be rotated to a position of registry with a discharge opening 14 in the cylindrical body 11 and which communicates with the disposal chute 15 for discharge of the fragmented particles into a jar 23 which contains sterilizing solution. Then the jar, with sanitized and fragmented items is said to be disposed of as ordinary trash. Solomons apparently is not intended to deal with soft waste items. Furthermore, the decontamination treatment is not conducted until after the fragmenting has been completed.

The waste from a physician's or dentist's office, and for which safe disposal is also needed, includes not only hard items such as needles, syringes and vials, but also soft items such as bandage material and rubber gloves. It is desirable to avoid the necessity of sorting the waste before disposal. The existing prior art equipment available in a size suitable for portable, desk-top or counter-top use in a comparatively small facility, cannot suitably handle such a variety of hard and soft waste materials.

SUMMARY OF THE INVENTION

The invention provides a method and apparatus for the collection and treatment of contaminated medical waste, including such solid items as syringes and needles, glassware, tubes, vials, culture plates and specimens, and disposable scalpels, and such soft and fibrous materials as gloves and masks. This invention permits the collection of such medical waste at the point and at the time of its generation in a container, which cannot be pierced or torn by the solid waste and in which the waste can be subsequently transported, pulverized and decontaminated for easy disposal on site.

The invention eliminates repeated handling of the medical waste and the associated danger of the inadvertent transmission of infectious diseases resulting from the handling of such waste. The invention permits these substantial safeguards to be enjoyed by those personnel working in smaller doctor's and dentist's offices and smaller clinics, which often do not have access to proper medical waste processing facilities, without unnecessary expense and duplication of apparatus.

The apparatus of the invention provides a separate portable processing chamber, with an integral means to treat medical waste, that can be used at locations remote from its power unit for the collection of medical waste and then moved to the remote location of the power unit to drive the waste-treatment means within the chamber for pulverizing and decontaminating the medical waste within the chamber without danger to medical or operating personnel.

The apparatus of the invention comprises a separate waste collection and processing assembly including a closable chamber for the collection, pulverization and decontamination of soft and hard medical waste. A rotating waste treatment system is rotatably carried within the chamber by bearings spaced on a supporting cylinder that is carried by the chamber bottom around a centrally located aperture through which the rotating system is driven. The rotating waste treatment system includes a plurality of pivotable blades that are carried by a rotating hub and have a configuration which, in cooperation with the chamber walls, provides for the effective disintegration, pulverization and blunting of solid waste, the cutting and mincing of non-solid waste, and the circulation and decontamination of the medical waste within the separate chamber. An inner surface configuration of the chamber provides a plurality of abutment or cutting surfaces coacting with the rotating blades to destroy the waste material and effectively direct and circulate the waste during its destruction and decontamination. Furthermore, the separate chamber is self-cleaning and provides collection means from which the destroyed and decontaminated infected waste material may be easily poured.

One embodiment of the apparatus of the invention further includes rigid fenders carried by the rotating waste treatment system in front of the pivotable blades and extending downwardly to a small clearance from the chamber bottom, to sweep soft waste from adjacent the rotating hub and prevent it from collecting and being carried under the rotating hub. The fenders can be raked in the direction of rotation and provide blade impingement surfaces to prevent the blades from pivoting forwardly in the direction of rotation past a radial line extending outwardly from their pivotal mountings. In addition, the fender-forming surfaces can extend upwardly on the rotating hub within the chamber to provide one or more rotating surfaces to fractionalize the breakable containers that carry used hypodermic needles and other solid waste.

A further embodiment of a rotating hub assembly of the apparatus of this invention includes a ring that extends outwardly from the rotating hub from its lower end to prevent soft waste from being carried under the hub.

The rotating hub assembly can also be provided with a pair of slots formed in its outer surface in which the blades are pivotally attached. The slots are preferably formed by a blade impingement surface adjacent the pivotal blade mounting, and extend away from the blade impingement surface in the direction opposite the rotation of the hub so that the blades can pivot rearwardly and be recessed partially within the hub in response to coming in contact with slow moving or semi-stationary objects. The blades are prevented from pivoting forwardly in the direction of rotation past their mountings by the forward blade impingement surface of the slot. The rotating hub assembly can further include a container-breaking surface comprising a spike or tooth member, equipped with a metal or carbide tip, protruding upwardly and outwardly adjacent the top surface of the hub.

In a preferred embodiment, the blades are pivotally secured within the slots formed in the outer surface of the rotating hub assembly by a rotatable axle pin extending downwardly through a bore provided through the hub assembly and a corresponding opening provided in the proximal end of the blade. The axle pin is secured therein and prevented from removing itself from within the bore by a fastener.

In addition, a radially inwardly extending surface can be provided in the waste treatment chamber sidewall which is positioned to direct waste material at the abutment and cutting surfaces for destruction by the coaction of said surfaces and the pivotable blades of the rotating waste treatment assembly.

In another preferred embodiment, a plurality of baffle means on the interior sidewall are located and adapted for more effective treatment of differing portions of the medical waste. In the preferred embodiment, one abutment bar is located at a first selected height above the floor of the chamber to preferentially act on non-soft medical waste adjacent the top of the chamber during operation, and a plurality of abutment bars are disposed along the interior sidewall of the chamber at a second selected height, which is lower than the first selected height, to preferentially act on, in cooperation with the cutting blades, soft medical waste adjacent the bottom floor of the chamber during operation.

A further alternative hub can be provided with an outer, generally frustoconical surface, an outwardly extending ring adjacent the lower edge of the hub member, and curved fins extending outwardly from the opposite sides of the outer surface of the hub and from near the top of the hub to the lower ring. This alternative hub may be used to replace the rotating hub assembly and, in operation, effect the complete cleansing and decontamination of soft medical waste.

In preferred apparatus of the invention, the waste treatment chamber is closed by a removable filter cap carrying a high efficiency particulate air filter that permits the escape of air and water vapor from the chamber during the operation while trapping aerosols and fine particles.

Preferred apparatus can also include means for supporting and retaining the waste treatment flask and any materials expelled from the waste processing chamber during operation, and for vibrationally isolating the waste treatment flask and driving motor from the apparatus enclosure.

Other features and advantages of the disclosed embodiments and methods of the invention will be apparent from the drawings and more detailed description of the invention that follows.

DESCRIPTION OF THE PREFERRED EMBODIMENT

Figure 1:
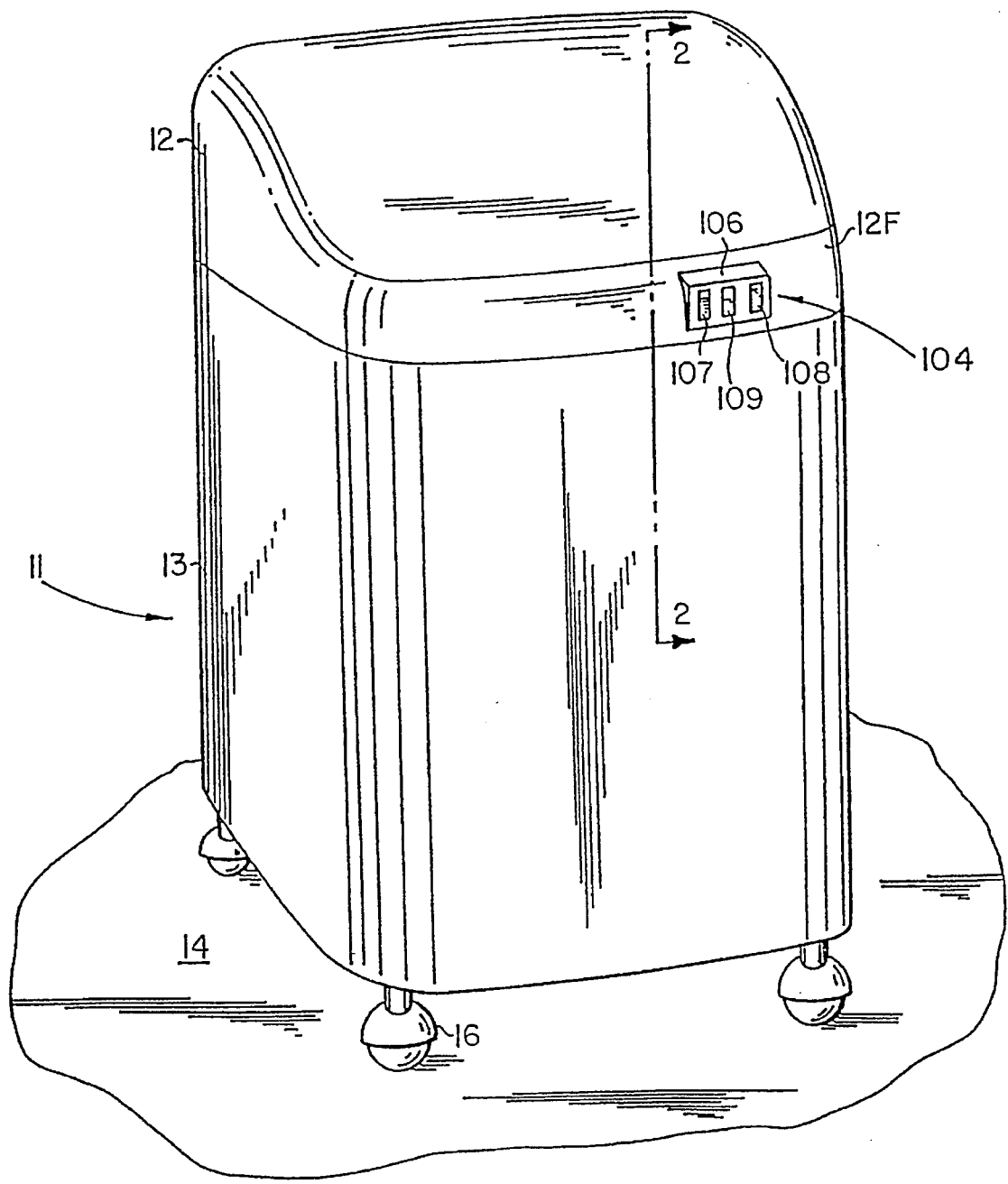
FIG. 1 is a pictorial view of a portable waste treatment device according to the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
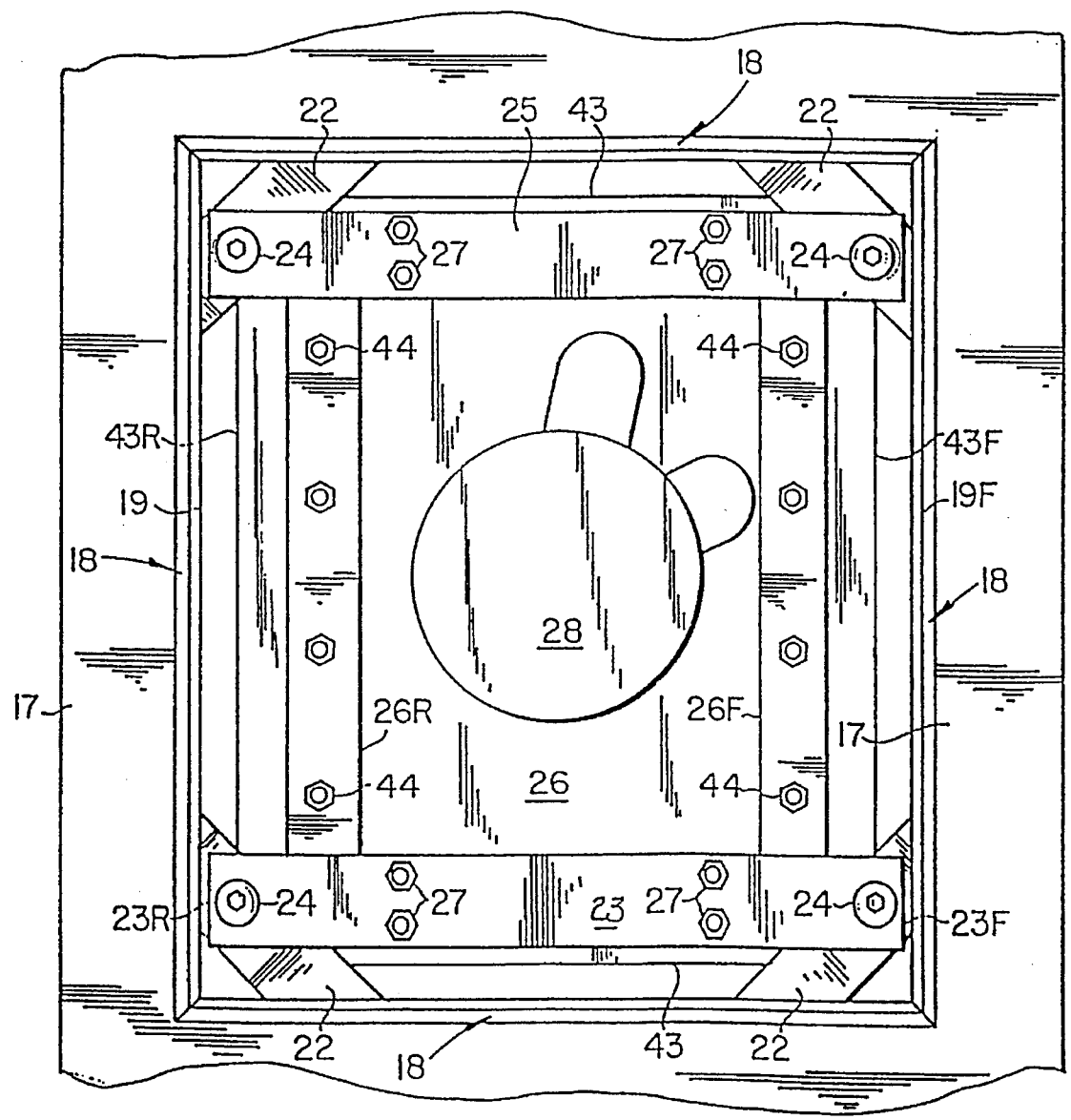
FIG. 3 is a fragmentary section taken at line 3—3 in FIG. 2 and viewed in the direction of the arrows.
Figure 4:
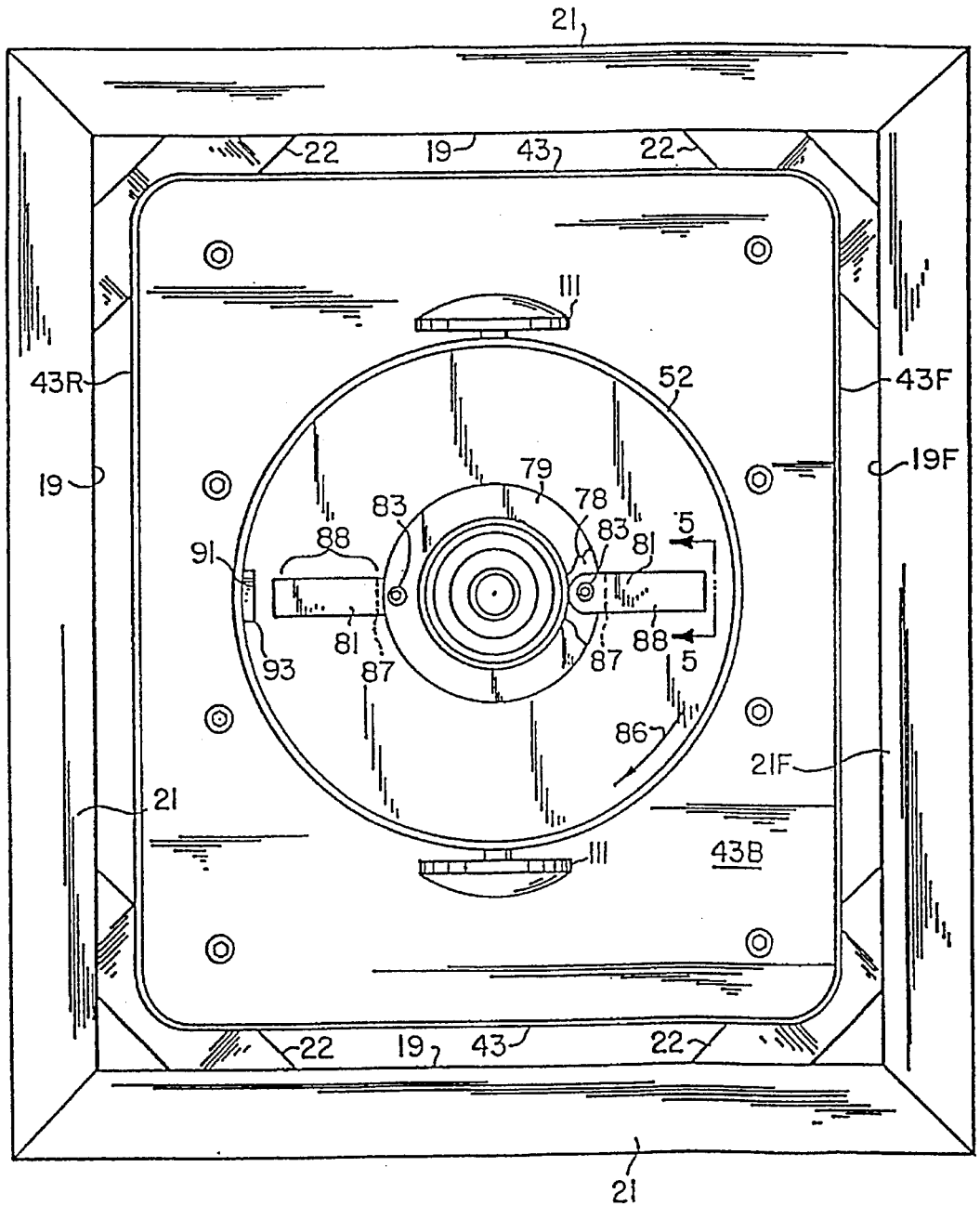
FIG. 4 is a section taken at line 4—4 in FIG. 2 and viewed in the direction of the arrows.

Referring now to the drawings in detail, and particularly FIG. 1, a floor-mounted, mobile unit 11 includes a main cabinet 12 mounted on the top of a cart 13 which is movable along the floor 14, being supported on four casters 16, one at each corner. Referring now to FIG. 3, and regardless of whether a mobile cart 13 or a stationary counter top is the site for the present invention, it will include a support 17 which, in the illustrated embodiment, is rectangular in shape, framing a central opening 18 in which the waste treatment device is mounted according to the present invention. For this purpose, a rectangular frame 19, typically metal, is provided with an outwardly extending perimetrical flange 21 (FIGS. 2 and 4) and is mounted on the support 17 and may be secured to it in any suitable manner. The portions of frame 19 and flange 21 that are at the front of the machine are designated 19F and 21F. Frame 19 has a gusset 22 welded to it at each of the four corners of the frame. An isolation strap 23 having a front end 23F and rear end 23R is mounted to the frame gussets 22 at their respective ends by means of isolator couplings 24. An identical strap 25 and mounting arrangement is provided at the opposite side of the frame 19.

A motor mount plate 26 is mounted on top of the two straps, with four fasteners 27 securing each side of the plate to each of the two straps 23 and 25. In the illustrated example, the fasteners are socket head cap screws with nuts. This motor mount plate is generally U-shaped as shown best in FIG. 2. The motor 28, having a standard C-face 29, is fastened to the bottom center of the plate 26 by four socket head cap screws 31. The motor shaft 32 extends up through a central aperture 33 in plate 26 and is provided with a slinger ring 34 immediately above the plate 26. The motor shaft has a standard square keyway to receive a standard square key 37 in coupling 38 to which the key is secured by set screw 39. The upper end of the coupling 38 is provided with a ½ inch square cross section at 41.

The outwardly turned front and rear flanges 26F and 26R, respectively, of the motor mount plate support the main cabinet 12. The cabinet has a front wall 12F, and a rear wall 12R and is molded in one piece of fiberglass reinforced plastic with a generally centralized tub portion 42 which is generally rectangular in configuration as shown by the front and rear walls 43F and 43R, respectively, and the sidewalls 43 in FIG. 4. The floor 43B of the tub is secured to the outwardly extending flanges 26F and 26R of the motor mounting plate by four fasteners 44 through each of the flanges, these fasteners typically being socket head cap screw and nut assemblies.

A hollow bulb gasket 46 is secured to the inside of the cabinet outer shell around the entire perimeter of the lower edge 47 of the shell. This gasket 46 lightly but sealingly engages the top surface of the support 17 entirely around the perimeter of the cabinet. However, it does not provide support for the cabinet since that is supported by the motor mount plate supporting the bottom 43B of the cabinet tub portion.

The flask assembly 51 of the present invention includes a flask lower housing 52 and flask top housing 53, both of which are symmetrical about the central axis 54. The flask lower housing has an outwardly turned upper circular flange 52U supporting an O-ring 56 which supports the circular bead at the bottom of the flask top housing. The top and lower housings are fastened together by over-center lever operated spring clamps 57 such as are available from Dzus Fasteners of West Islip, N.Y. 11795. The bottom of the flask lower housing has four circularly spaced feet 58 which are received in sockets 59 in the floor 43B of the cabinet tub portion. These feet support the flask assembly in the cabinet tub. They also prevent the flask assembly from rotating in the tub.

An impeller assembly 61 is mounted in the flask assembly. It is located and supported by a bearing mount cylinder 62 which is welded to the bottom of the flask lower housing at 63 around the central opening 64 in the flask bottom. This bearing mount cylinder receives the lower ball bearing assembly 66 and the upper ball bearing assembly 67. The inner race of each of these ball bearing assemblies fittingly receives outer cylindrical surfaces of the impeller shaft 68 which has an octagonal internal spline or socket at 69 received on the square upper end of the coupler 38. The upper portion of the impeller shaft has a sleeve 71 pressed thereon above the inner race of the upper bearing 67. This serves to engage a lip seal 72 which is secured in the outer race receiving bore of the impeller bearing mount cylinder 62. The upper end of shaft 68 is threaded at 73 and threadedly receives thereon the top 74 of the impeller which extends from the top down to the slinger flange 76 at the bottom and which is immediately above the bottom of the flask lower housing.

Figure 5:
FIG. 5 is an end view of a blade taken at line 5—5 in FIG. 4 and viewed in the direction of the arrows.

The cylindrical wall 77 of the impeller has two additional circular flanges above the slinger flange 76. These are the blade support flange 78 and the blade hub cover flange 79. Two blades 81 are mounted in the annular groove 82 between the flanges 78 and 79 and pivotally secured in place by the pins 83 which are shoulder bolts screwed into the flange 78. The shape of these blades can be observed in FIG. 4 and FIG. 5. The blades are driven in the clockwise direction of arrow 86 in FIG. 4. Although the hub area of the blade is rectangular as shown in FIG. 5, the blade is tapered beginning at a line 87 (FIG. 4) to provide a sharp leading edge 88 while the trailing edge of the blade 89 is the full height of the hub area of the blade. The blade is preferably made of steel but tungsten carbide may also prove suitable.

A "baffle" bar 91 is mounted on the inside upstanding cylindrical wall of the flask lower housing and extends up from near the bottom to a top edge 92. Thus, it presents a 90° angle edge 93 facing the materials as they are driven around by the impeller blades moving in the clockwise direction of arrow 86. Due to the inclination of the lower face of the blades 81 downward from the front or leading edge toward the rear or trailing edge, as the blades 81 rotate the trailing edge of each is closer to the bottom of the flask than is the sharp leading edge. This drives the waste materials downward and thus assures that they will be aggressively treated by the baffle bar 91 during operation.

A removable flask cap 96 is provided in the central opening 97 at the top of the frustoconical surface of the flasktop housing. This cap 96 has a tapered wall 98 so as to be manually insertable to the point of a snug fit, but can be readily removed manually, if desired, by means of the outwardly directed circular flange 99 at the top of the cap. The cabinet is provided with a lid 101 which is hinged to the upper rear wall 12R of the cabinet by adjustable hinges 102 such as the 500 Series marketed by Southco, Inc. of Concordville, Pa. 19331. These hinges are adjustable so that the lid can be raised at the front end edge in the direction of arrow 102a and can remain in virtually any position up to vertical. The underside of the lid has an inwardly projecting bulge 103 therein which, when the lid is closed, engages the flask cap 96 and assures that the cap will remain securely closed in place on the flask top housing. A bulb gasket may be provided around the perimeter of the cabinet lid to seal against the cabinet top during operation.

Figure 6:
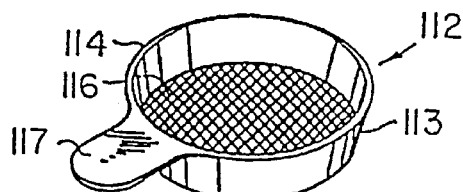
FIG. 6 is a perspective view of a strainer plug used in the practice of the invention.

Referring to FIG. 6, a strainer cap 112 is shown. It is similar to cap 96, having a tapered wall 113 and perimetrical top flange 114 but, instead of a solid bottom, the bottom 116 is a screen. It may also have a handle tab 117 at the top flange.

Referring again to FIGS. 1 and 2, a control group 104 is provided on a boss 106 at the front of the cabinet and includes a momentary contact "ON" switch 107, and "EMERGENCY STOP" switch 108, and a pilot light 109 illuminated when the operating cycle is in progress. These are associated with suitable electrical circuitry to control the motor as desired. The circuitry is not shown herein as it may be conventional and well within the skill of the art.

Referring again to FIG. 4, a pair of T-type handles 111 may be provided on the side of the flask lower housing for a purpose which will be described now.

Mode of Operation

The flask assembly is removable from the main cabinet by simply lifting the cabinet lid and lifting the flask assembly out of the cabinet by use of the T-handles, one in each hand. The flask assembly can be easily lifted off the coupler and moved to whatever site location is convenient for depositing medical waste material therein, which is typically wherever such material is being generated. Of course, if the unit is mounted on a moveable cart as in FIG. 1, the cart can be simply pushed to the site without removing the flask assembly from the cart. With the top cap 96 pulled out of the top of the flask assembly, the waste material can be simply dropped into the flask assembly through the opening 97. The opening has a sufficient diameter, four inches, for example, to readily receive syringes, bandage material, rubber gloves, culture plates and vials, for example. Such waste materials can be dropped directly into the opening 97 as they are produced, or they can be put into another container and then transferred later to the flask. For example, as a bandage is removed from a subject, the bandage materials can be placed directly into the flask. When the flask assembly has been filled to a level about even with the top of the flask lower housing or bowl 52, and if the flask assembly is separate from the main cabinet, it can then be returned to the main cabinet and placed on the cabinet tub bottom with the four feet 58 aligned within the pockets 59. Simultaneously the impeller shaft socket is received on the coupler square 41. Water is then poured through the top opening 97, a pouch of decontaminant is added, and the top cap 96 is installed and the cabinet lid is closed. The start switch 107 is then pushed past the lid and may thereupon be locked by an automatic electrically operated lid latch (not shown). The motor is now energized which drives the impeller, which in turn drives the blades in a clockwise circular path as shown by reference arrow 86 in FIG. 4 around the impeller axis. As the blades are driven, they begin to cut-up the waste material in the housing.

Although the materials provide some resistance to the action of the blades, the combined effects of the sharp leading edges 88 of the blades and of centrifugal force keep the blades deployed in a substantially radially outward, extending direction to continue to cut up the waste material. As this occurs, the slinger flange 76 at the bottom of the impeller assembly keeps the material moving outwardly and upwardly around the curved outer portion 55 of the flask lower housing wall 52. Thus, the material is kept moving in a path outward and upward along the wall and then back down into the cutting path of the blades. In addition, the presence of the vertical block (baffle) 91 provides an abutment which, to materials moving in the clockwise direction, presents a relatively sharp edge. Baffle 91 also inhibits the free circular flow of material around the inner wall of the flask lower housing, tending to knock or direct the material back into the cutting path of the blades. Thus, the baffle 91 facilitates the destruction of sharp items and facilitates the cutting and tearing of soft materials.

The processing continues as long as desired until it is either stopped by expiration of the "run" period of an automatic timer, or is manually stopped by pushing the emergency stop pad 108 to simply end the desired cycle. The pilot light serves as an indicator that a cycle is in process. This light may remain on for several minutes after the processing is complete in order to indicate to the operator that it is not yet time to open the lid because, among other possible reasons, the contents may not have yet settled.

When the pilot light goes out, the operator can then open the lid, grip the T-handles, pull the flask assembly out of the tub of the main cabinet, and transport the flask to a sink. The cap 96 is then removed and replaced by the strainer 112 in the opening 97. Then the flask assembly is inverted in the sink, and the decontaminant solution, together with any other liquids which were contained in the waste material are drained into the sink. Then the flask assembly is righted and moved over to a solid waste receiver bucket or bag or the like, and the processed waste materials are dumped into the receiver for subsequent disposal in a conventional waste container.

As an alternative procedure, instead of using the strainer, the flask assembly can be dumped, liquids and solids simultaneously, into a disposable bag containing a liquid-absorbent gel compound. In this scenario, the flask is righted and ready for return to the waste generation site for collection of more waste.

With a machine built according to the present invention, in addition to the mincing action on materials, needles are bent and blunted as they are driven into the baffle 91. If it is ever desired to do so, the flask can be washed out without taking it apart, just as one could wash out a vase or bowl. If ever desired, such as for servicing interior components, the flask upper and lower housing can be separated by releasing the spring clamps 57. After servicing, they can be re-assembled, clamped together, and the flask assembly can be returned to the waste generation site for use again as described above.

As an example, the chamber-forming flask components can be made of spun stainless steel. Many of the more dense components, such as the impeller bearing mount cylinder, the impeller shaft, and the impeller itself, can be stainless steel investment castings. For a flask assembly that will hold and process approximately one-two gallons of medical waste materials in their final processed state, a drive motor of two horsepower is useful to complete a processing of that much material within a two to three minute cycle. A rotational speed of about 3450 r.p.m. is advisable for effective destruction of the solid and soft medical waste identified above. Examples of suitable decontaminant solutions are a one ounce package of "A-33" dry decontaminant powder as marketed by Airkem Professional Products of St. Paul, Minn. and an Iodophor disinfectant compound sold by Ecolab, Inc. at Minneapolis, Minn. under their trade name "Mikroklene". Dumping of treated waste from the flask can be into a plastic bag of appropriate size and at least 3 mm. membrane, and preferably an eight gallon, double ply plastic bag, which contains a polymeric absorbent powder which develops a gel as it absorbs the liquid. The bag preferably has a drawstring for convenient handling and can be placed in a conventional trash or garbage container. Although the description refers to a one-gallon flask or chamber, it should be appreciated that the present invention can be applied to larger or smaller size apparatus.

Figure 8:
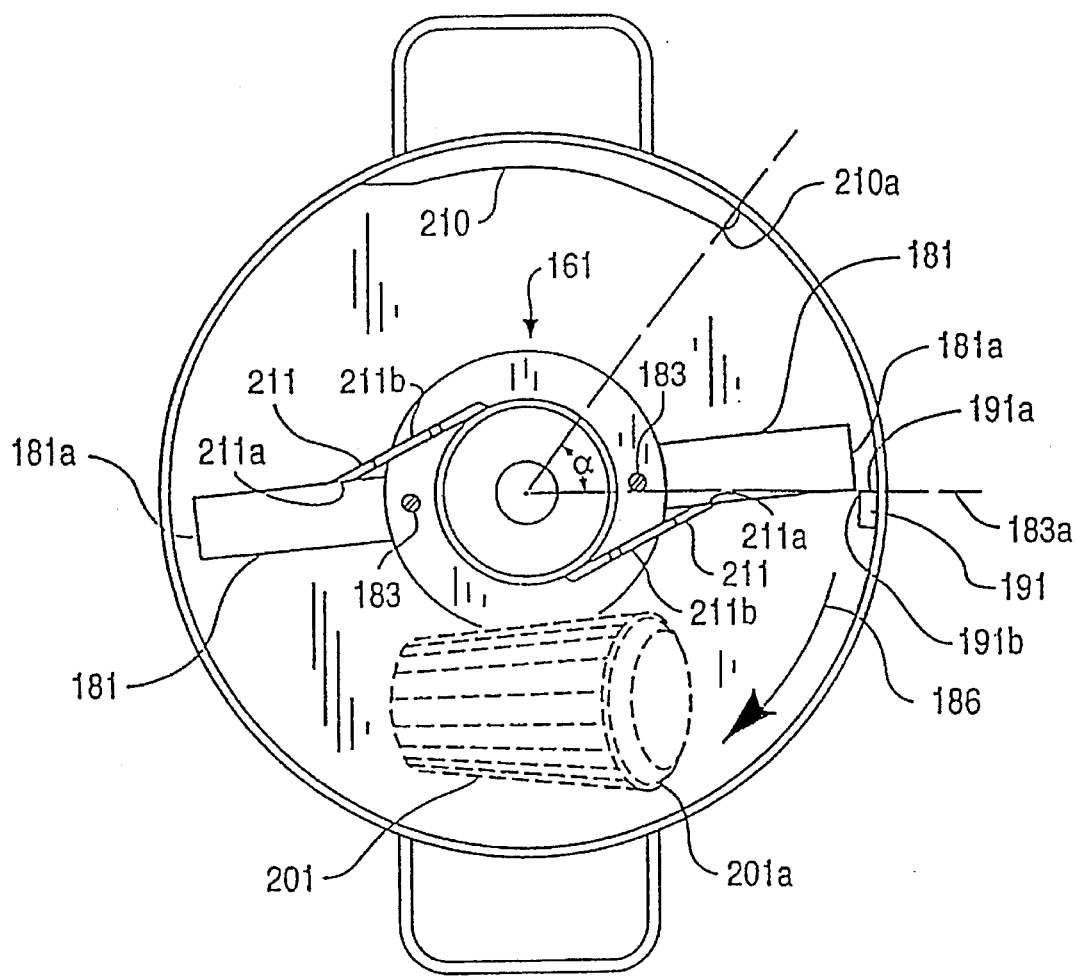
FIG. 8 is a view looking downwardly into the apparatus of FIG. 7 at line 8—8 of FIG. 7, showing in phantom lines a breakable container for the collection of medical waste.

The invention can further include the use of an imperforable but breakable container particularly adapted to receive and contain used and possibly infectious, sharp solid waste, such as used hypodermic needles, vials, culture plates, and the like. Such a container 201 (FIG. 8), or containers, may be located at the locations in which blood samples are taken or injections are given for the collection of the possibly infectious used hypodermic needles. Container 201 for such used medical waste is preferably formed or molded from a material which cannot be perforated by such sharp, solid waste as used hypodermic needles but which will break or fractionate or shatter when impacted. A preferable material is glass or clear molded polystyrene of the type commonly used for inexpensive drinking utensils. The container 201 may be molded in a glass- or cup-like shape as shown in FIG. 8, with thin walls on the order of about 1/32 to about 1/16 inch thick to provide safety in handling of its contents after collection. Preferably, a molded polystyrene cover with downwardly turned lip adapted to snap fit over the open top of the container 201 can provide the container 201 with an imperforable but breakable cover (indicated at 201*a* on FIG. 8) for the further safe handling of the container's contents after its collection. A screw-on lid that can be threadably secured to the container may also prove suitable.

Figure 2:
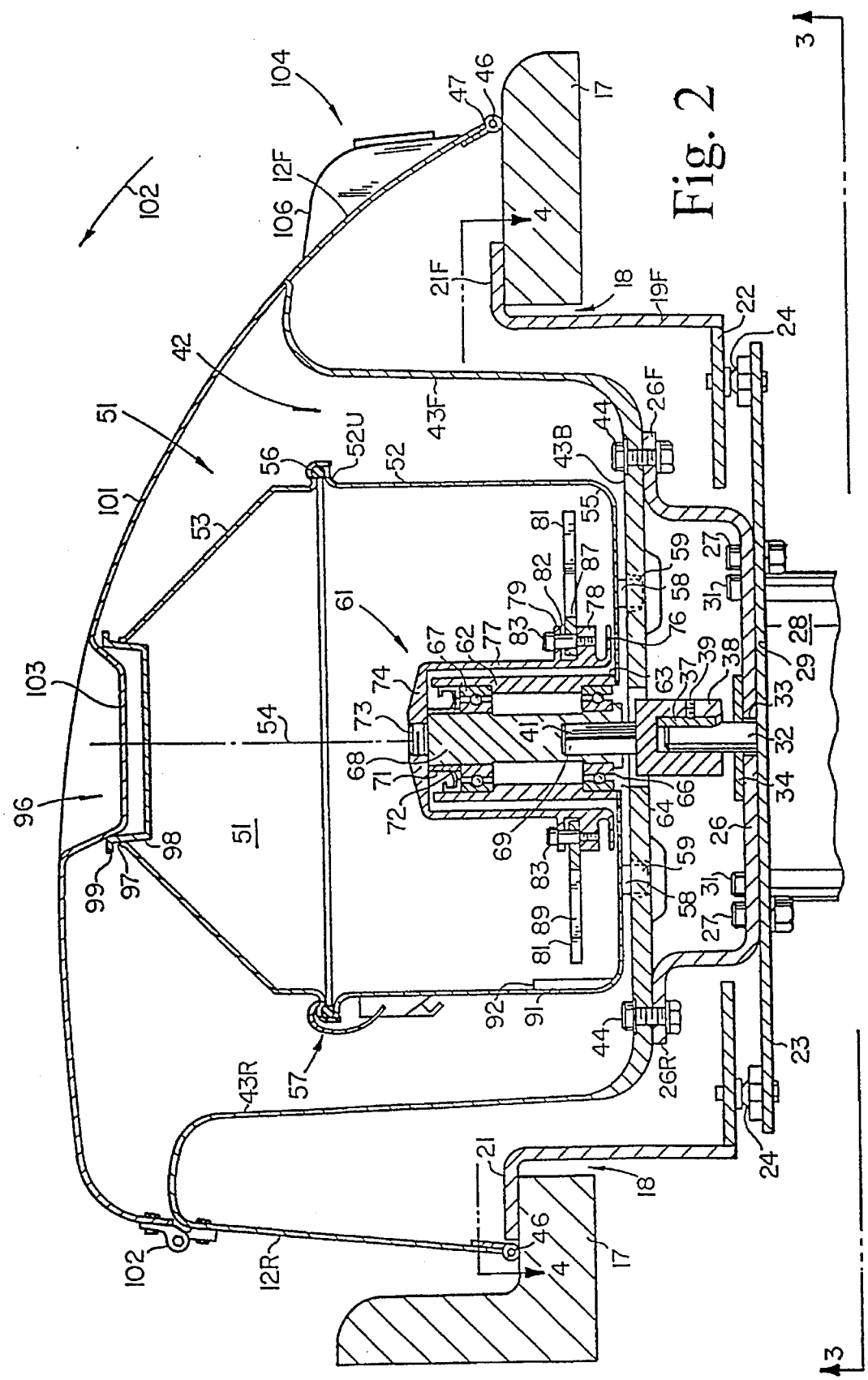
FIG. 2 is an enlarged fragmentary vertical section through a portion of the cabinet taken at line 2—2 in FIG. 1 and viewed in the direction of the arrows and showing some interior details.
Figure 7:
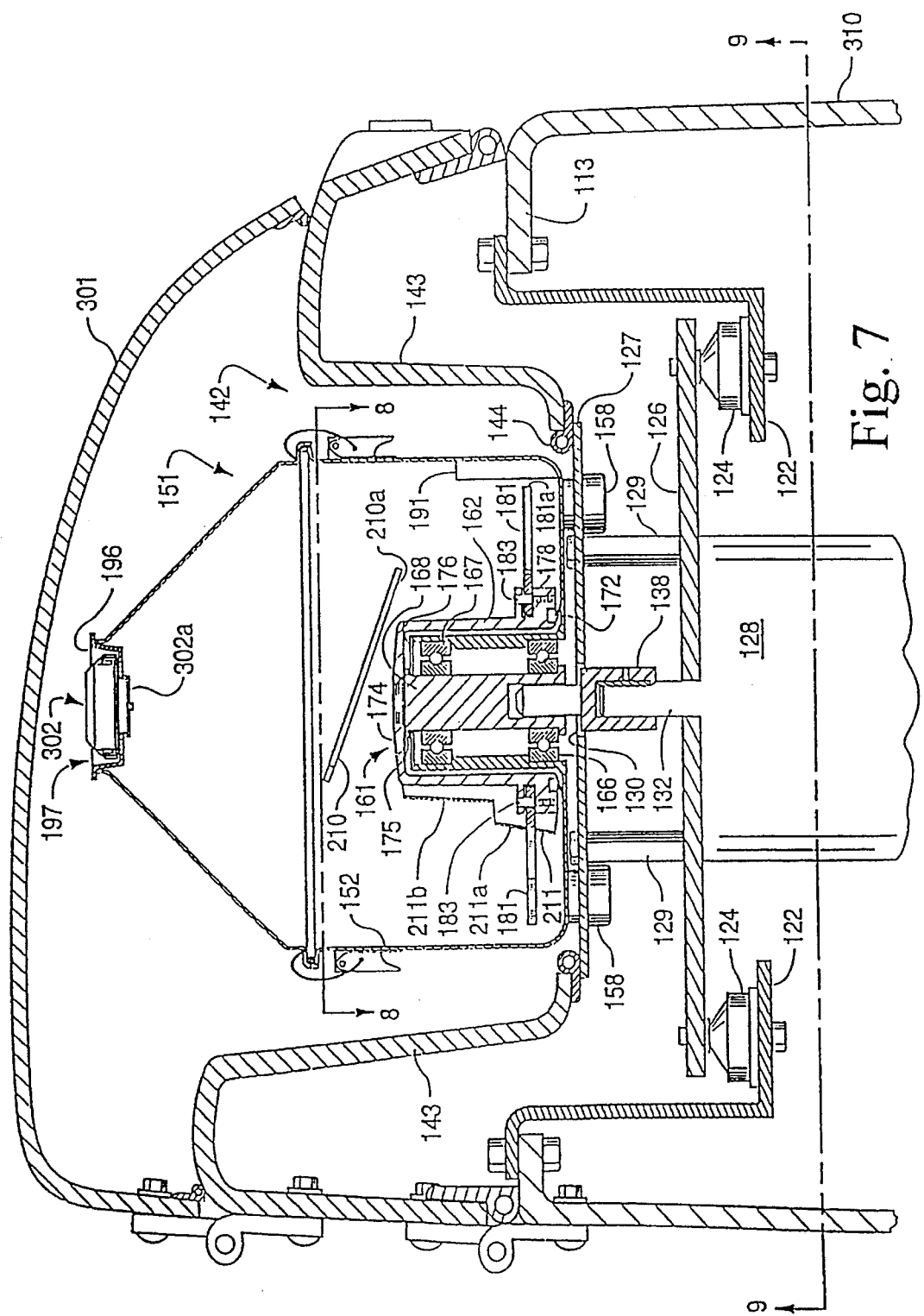
FIG. 7 is a cross-sectional view of a further preferred embodiment of the invention, taken at a central plane along line 2—2 in FIG. 1.

Following the collection of solid medical waste in container 201, the entire container may be carried to and inserted in the waste treatment chamber of the type shown in FIGS. 2 and 7 for disposal. The container 201 carrying the solid medical waste may be inserted through the opening to the chamber (97 in FIG. 2 and 197 in FIG. 7) for destruction. As indicated in phantom lines in FIG. 8, container 201 will be impacted by one of the rotating surfaces of the rotating assembly within the chamber and will be shattered or fractionated, spilling its contents into the interior of the waste destruction chamber. In the chamber, used hypodermic needles and syringes and the pieces of the container 201 will be driven around the chamber while being impacted by the pivotable blades 81, 181, and impacting the abutment surfaces of the abutment bars 91, 191, thereby breaking the larger pieces to small minced solid waste, blunting the tips and sharp edges of the needles, syringes, scalpels and the like, and scrubbing the surfaces of the waste materials with decontaminant.

FIG. 7 is a cross-sectional view of another embodiment of the waste treatment apparatus of the invention and FIG. 8 is a view downwardly into the interior of the medical waste treatment chamber of the FIG. 7 apparatus.

The apparatus of FIGS. 7 and 8 is in most respects identical to that shown and described above. Unlike the apparatus shown in FIG. 2, however, the underside of the hinged lid 301 of the apparatus shown in FIG. 7 does not include an inwardly projecting bulge, like bulge 103 in the apparatus of FIG. 2 which engages the flask closure 96 to ensure that the closure 96 would remain in place in the chamber opening.

Figure 9:
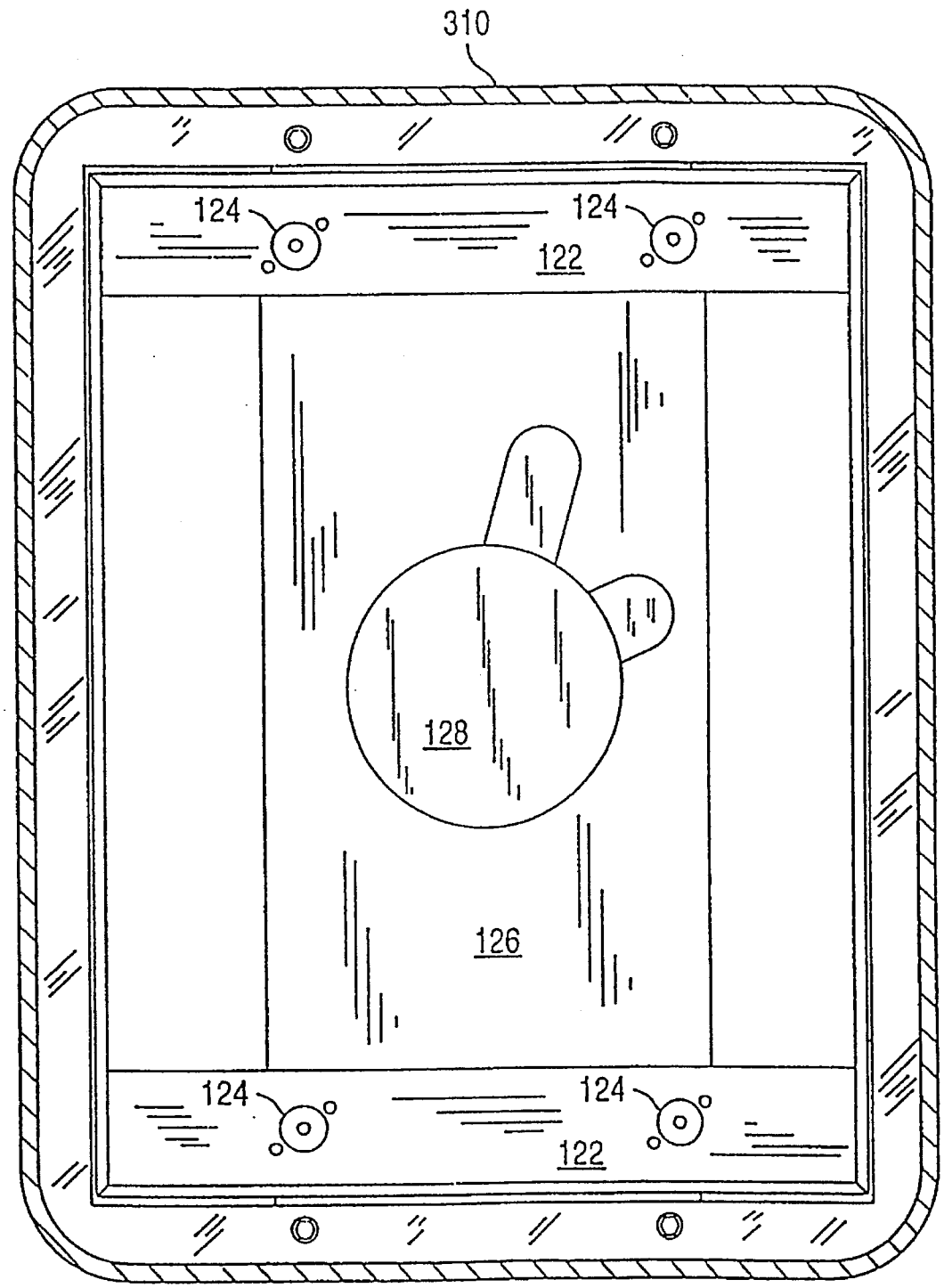
FIG. 9 is a cross-sectional view taken at line 9—9 of FIG. 7 and viewed in the direction of the arrows.
Figure 10A:
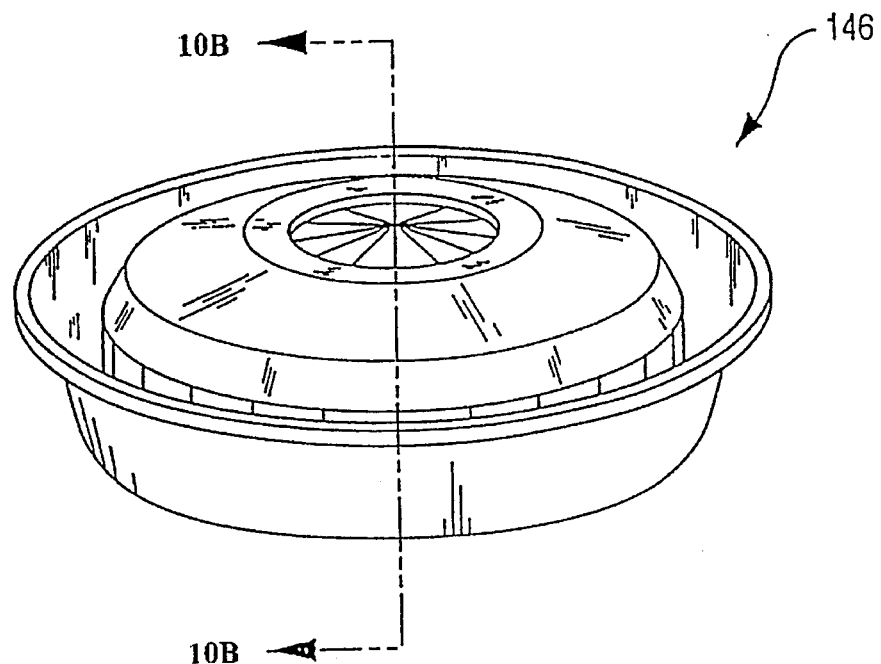
FIG. 10A is a perspective view of the waste treatment chamber closure.
Figure 10B:
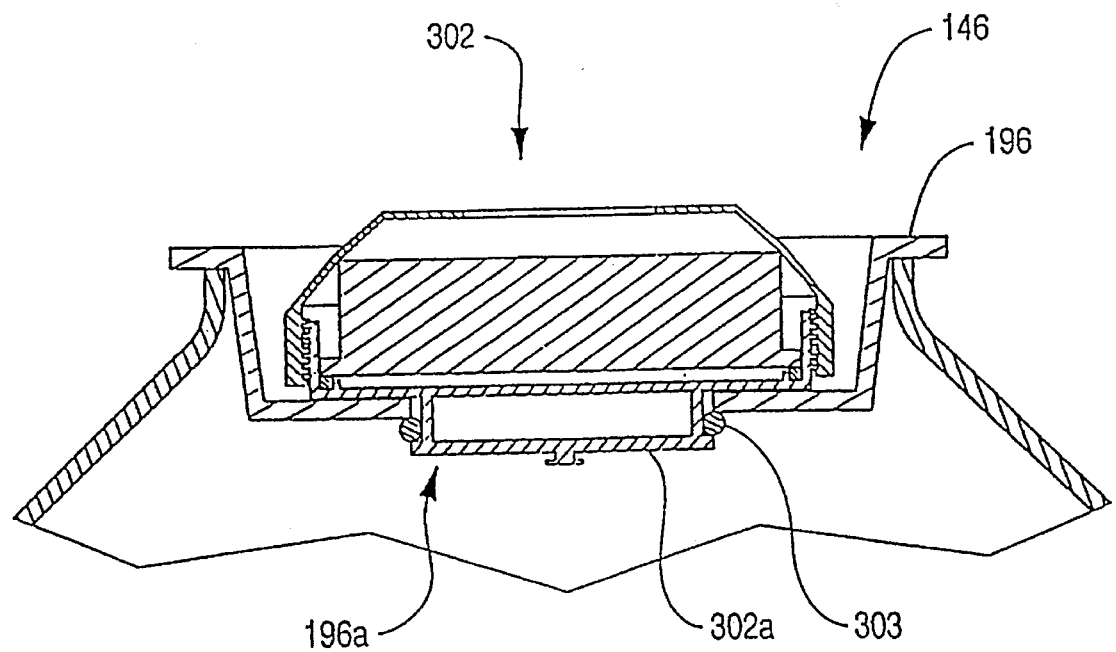
FIG. 10B is a cross-section of the waste treatment chamber closure taken at line 10B—10B of FIG. 10A.

In the apparatus of FIGS. 7–10, the closable chamber opening 197 is closed by a removable filter cap 196, as shown in greater detail in FIGS. 10A and 10B. Removable filter cap 196 carries a high-efficiency particulate air filter 302 of the type sold by the 3M Company as their filter Number 7255. The particulate air filter 302 is fitted to an opening 196*a* in the removable filter cap 196, which is otherwise identical to the cap 96 shown in FIG. 2. The particulate air filter 302 extends downwardly through the opening 196*a* formed in the base of cap 196 and is held in the cap by an O-ring 303 fitted over the filter portion 302*a*, which not only holds filter 302 to cap 196 but also seals the interface between the filter 302 and the cap 196. The O-ring retention of particulate air filter 302 thus permits an inexpensive method of fastening and sealing the particulate air filter 302 to the cap 196 and its simple replacement, if necessary. Particulate air filter 302 permits the passage of air and water vapor from the chamber during operation of the waste treatment apparatus but prevents aerosols and fine particles from escaping. Heat generated by the waste treatment within the chamber creates an expansion of the air and water vapor within the chamber which would tend to dislodge cap 196 from opening 197 in the absence of the particulate air filter 302.

As shown in FIGS. 7 and 8, a preferred apparatus of the invention includes a radially extending surface 210 on the chamber sidewall 152. Surface 210 is positioned to direct medical waste materials moving within the chamber to expose it to the coaction of the abutment bar 191 and pivotal blades 181. As shown in FIGS. 7 and 8, the radially extending surface 210 is preferably a ribbon of stainless steel having a thickness on the order of about 3/16 to about 3/8 of an inch and welded (or otherwise fastened) to the sidewall 152 of the chamber in a downwardly extending direction from adjacent the upper portion of sidewall 152 to adjacent the central portion of chamber sidewall 152 so that waste materials will, for example, leave the terminal portion 210*a* with an increased velocity directed at abutment bar 191.

As indicated above and shown in FIG. 8, abutment bar 191 provides an abutment surface 191*a* extending radially inwardly from the container sidewall 152 against which the rotating waste materials impinge. Abutment bar 191 further provides a cutting edge at corner 191*b* which is located only a small clearance distance from the ends 181*a* of the blades 181, as indicated in FIGS. 7 and 8. The coaction of blade ends 181*a*, the abutment surface 191*a* and cutting edge 191*b* of abutment bar 191 cut and tear soft medical waste material, such as those described above, into small pieces, and fractionate and dull solid medical waste of the type described above into a generally minced condition. It will be noted that the radially extending surface 210 tends to direct materials adjacent the abutment bar 191 for exposure to this coaction. In preferred embodiments of the invention, the terminal portion 210*a* of the material deflector 210 is located "upstream" of the abutment surface 191*a* and cutting edge 191*b*, and the included angle $\alpha$ between its termination portion 210*a* and the surface 191*a* of the abutment bar lies in the range of 40°–90° to avoid entrapment and lodging of the waste material therebetween.

The apparatus shown in FIGS. 7 and 8 further includes a pair of fenders 211 (only one of which is shown in FIG. 8) affixed to the rotatable hub 161 adjacent the pivotable mountings 183 for the waste treating blades 181 and extending downwardly below the blade support flange 178 to a small clearance above the chamber bottom. The fenders 211 thus prevent soft medical waste material, such as cloth and plastic dressings and rubber gloves, from collecting under the blade supporting flange 178 where they may slow the rotation of the rotating hub 161 and rob the rotating waste treatment assembly of power. Fenders 211 sweep such waste material outwardly and impel it against the container sidewalls 152 for impingement by the abutment bar 191 and pivotable blades 181 and destruction thereby.

As shown in FIG. 8, placement of the rigid fenders 211 adjacent the pivotable mountings 183 of the waste treating blades 181 can provide surfaces 211*a* that impede the rotation of the waste treating blades 181 in the direction of rotation, as shown by reference arrow 186, forwardly of a radial line 183*a* extending outwardly from their pivotal mountings 183. If the pivotable blades 181 pivot in the direction of rotation in a direction forwardly of a radial line 183*a* from the center of the rotating head 161 through their pivotable mountings 183, the blades will tend to draw waste material toward the center of the chamber.

As shown in FIG. 8, the fenders 211 are raked to form a forwardly facing acute angle adjacent the blade supporting hub 178 to reduce drag and assist the action of fenders 211 in sweeping waste material toward the sidewalls 152 of the chamber and the abutment bar 191.

As further shown in FIGS. 7 and 8, fenders 211 may be formed by a pair of metal members that extend upwardly along the rotating hub 161 into the central portion of the chamber to provide an upper rotating edge 211b. The rotating edge 211b can be adapted to fractionalize larger breakable containers 201 which may be inserted within the waste treatment chamber.

As shown in FIG. 7, the rotating hub assembly 161 includes a seal-carrying groove formed in the lower surface of the rotating blade flange 178 and carries a rotating lip seal 172 between the bottom of the rotating blade hub portion 178 and the bottom of the chamber-forming flask assembly 151. The rotating V-ring seal 172 in cooperation with a V-ring seal 175 compressed between the top 174 of the impeller hub and a bearing protection plate 176 protect bearings 166 and 167 from chamber contents.

Figure 11:
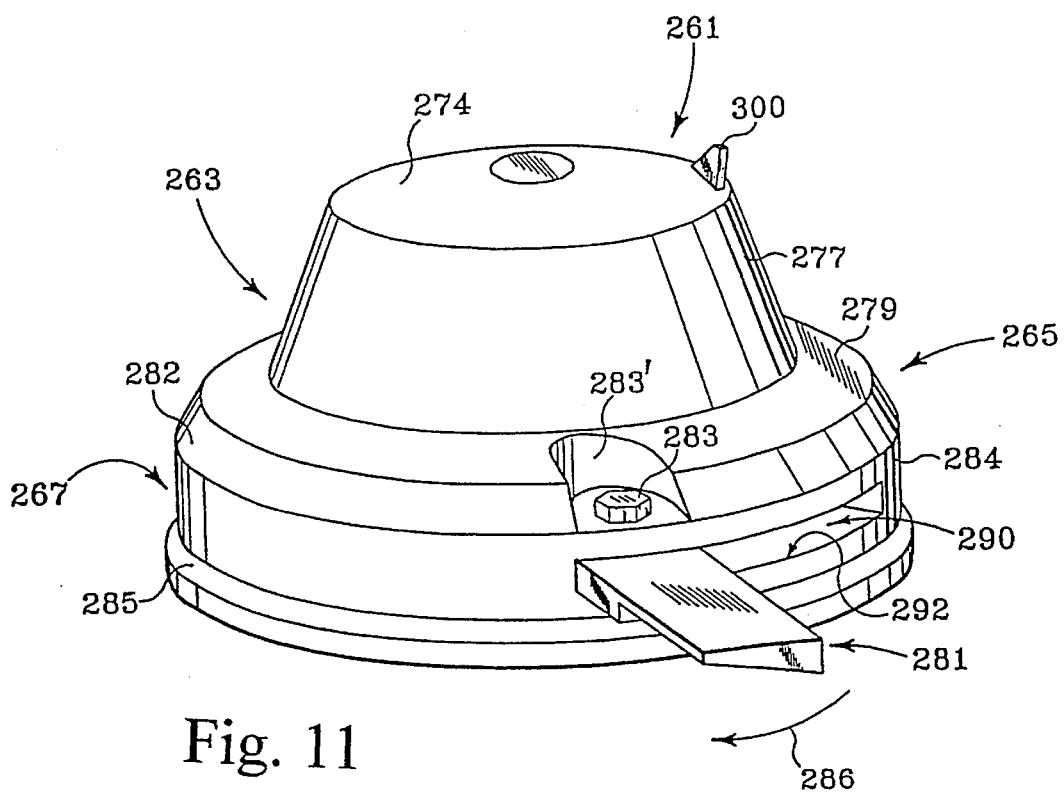
FIG. 11 is a perspective view of a further embodiment of a rotating hub assembly of this invention.
Figure 12:
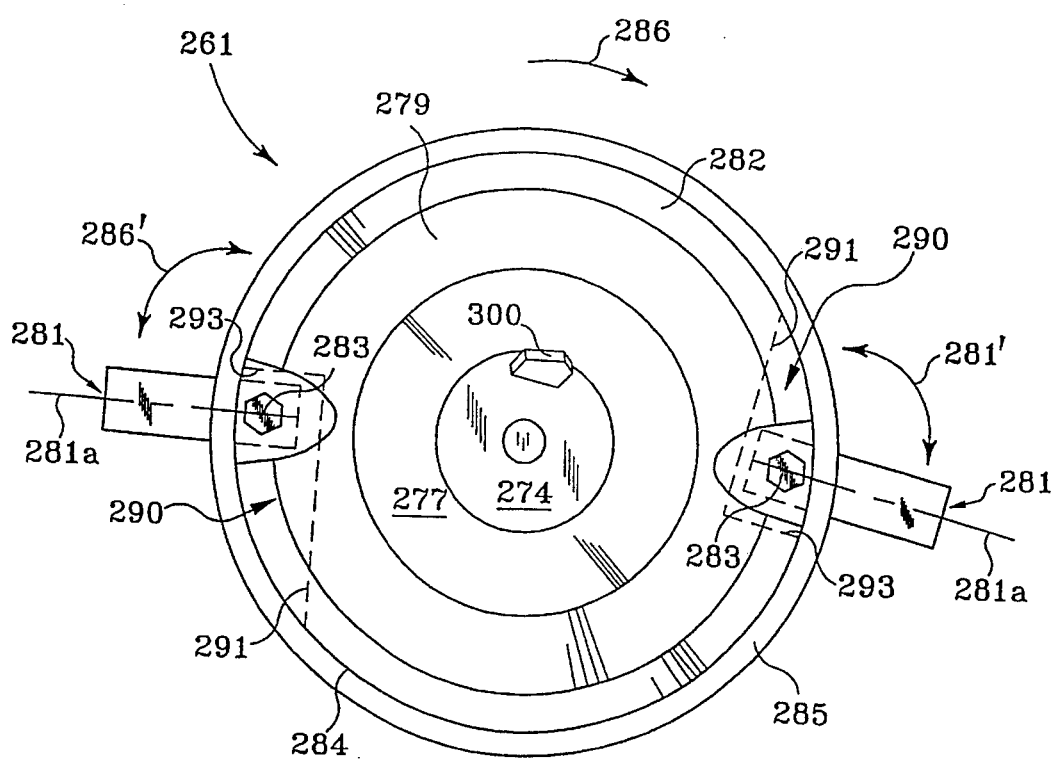
FIG. 12 is a top view of the rotating hub assembly of FIG. 11.

A further preferred impeller hub assembly 261 suitable for use with this invention is shown in isolation in FIGS. 11 and 12. Impeller hub assembly 261 is located and supported within the flask housing in identical fashion as impeller assemblies 61, 161 shown and described in relation to FIGS. 2 and 7, respectively. Hub assembly 261 is formed with an upper portion 263, a middle portion 265, and a lower portion 267. Hub assembly 261 further includes a ring 285 disposed at the lowermost portion 267 to prevent soft medical waste from being carried under hub 261 while it rotates. Upper portion 263 preferably includes an inclined wall 277 and lower portion 267 preferably includes a cylindrical or vertical wall 284. An annular shoulder 279 is disposed normally to the axis of rotation of hub 261 and an inclined frusto-conical wall 282 is disposed in middle portion 265 interconnecting shoulder 279 and vertical wall 284.

A pair of blades 281 (only one blade is shown in FIG. 11) are pivotally mounted to the hub 261 at diametrically opposed locations on the sides of the hub 261 adjacent its lower portion 267 within recessed slots 290 provided in wall 284. Blade 281 is identical to blades 81, 181 shown and discussed above. Blades 281 are pivotally secured by pins 283 formed by shoulder bolts extending through a receiving hole (not shown) provided near the inner or proximal end of the blade 281 and screwed into the lower surface 292 of slot 290. Bolts 283 are received in a recessed area 283' provided in the middle portion 265 of hub 261.

As shown in FIG. 12, slots 290 are formed in the sidewall 284 of hub 61 and extend inwardly toward the center of hub 261. Slots 290 include first forward impingement surfaces 293 and a second rear impingement surfaces 291. When the hub 261 is rotating in the direction shown by reference arrow 286 (clockwise), the pivotal blades 281 are urged to pivot outwardly along path 281' by centrifugal force to the extended position shown in FIG. 12. The blades 281 are prevented from pivoting forwardly in the direction of rotation (arrow 286) substantially past a reference line 281a extending radially outwardly from their pivotal mountings by the forward impingement surface 293 engaging the leading edge of blade 281. Upon contact with stationary or more slowly moving waste material, the blades 281 can pivot rearwardly along reference path 281' where they can be partially received within slots 290 and the following edge of blade 281 impinges upon the second rear impingement surface 291 of slot 290.

Hub 261 shown in FIGS. 11 and 12 can further include means for breaking waste-carrying containers introduced into the waste treatment chamber. Such container-breaking means can comprise a spike or tooth-like member 300 equipped with a carbide metal tip and protruding upwardly and outwardly adjacent the outer edge of top surface 274 of the hub assembly 261. Spike 300 is effective in disintegrating waste-carrying containers made of thin polystyrene such as container 201 described above.

Figure 13:
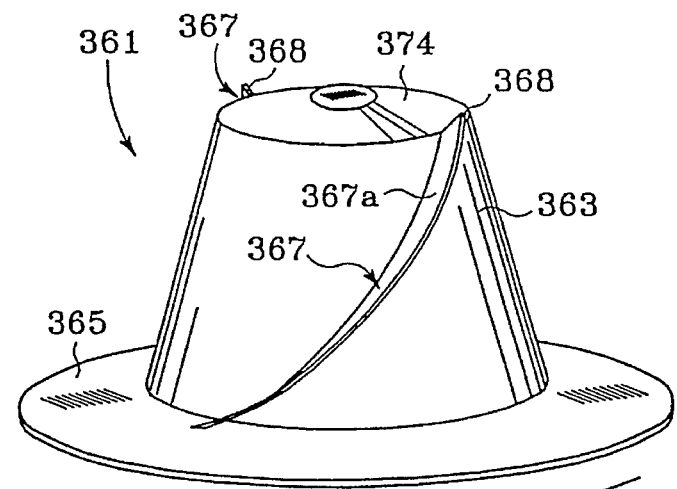
FIG. 13 is a perspective view of an alternative rotating hub provided in this invention.

This invention provides a further alternative hub 361, shown in FIG. 13. The alternative hub 361 may replace the rotating hub assemblies described above when it is desirable to simply wash or decontaminate the soft medical waste with a decontaminant prior to its disposal. Alternative hub 361 includes a generally frustoconical outer surface 363, a pair of fins 367 extending outwardly from the outer surface 363 of the hub 361, and a ring 365 extending outwardly from adjacent the lower edge of the outer surface 363. Ring 365 prevents the soft medical waste from being carried under the rotating hub 361, and also prevents waste materials from sitting idly on the bottom of the chamber during operation and thereby evading the washing and decontaminating action of hub 361. Fins 367 are disposed diametrically on opposite sides the outer surface 363 of hub 361 and partially form spiral-like surfaces 367a from adjacent the top surface 374 of hub 361 to the lower band 365. Each fin 367 has an upper tip 368 extending vertically above the top surface 374 of hub 363 adapted to tear open plastic refuse bags that are commonly used to tote soft medical waste, and to prevent materials from remaining idly on the top surface 374 of hub 361 while in operation. Thus, hub assembly 361 can effect the medical cleansing and disinfecting of soft medical waste.

Figure 14:
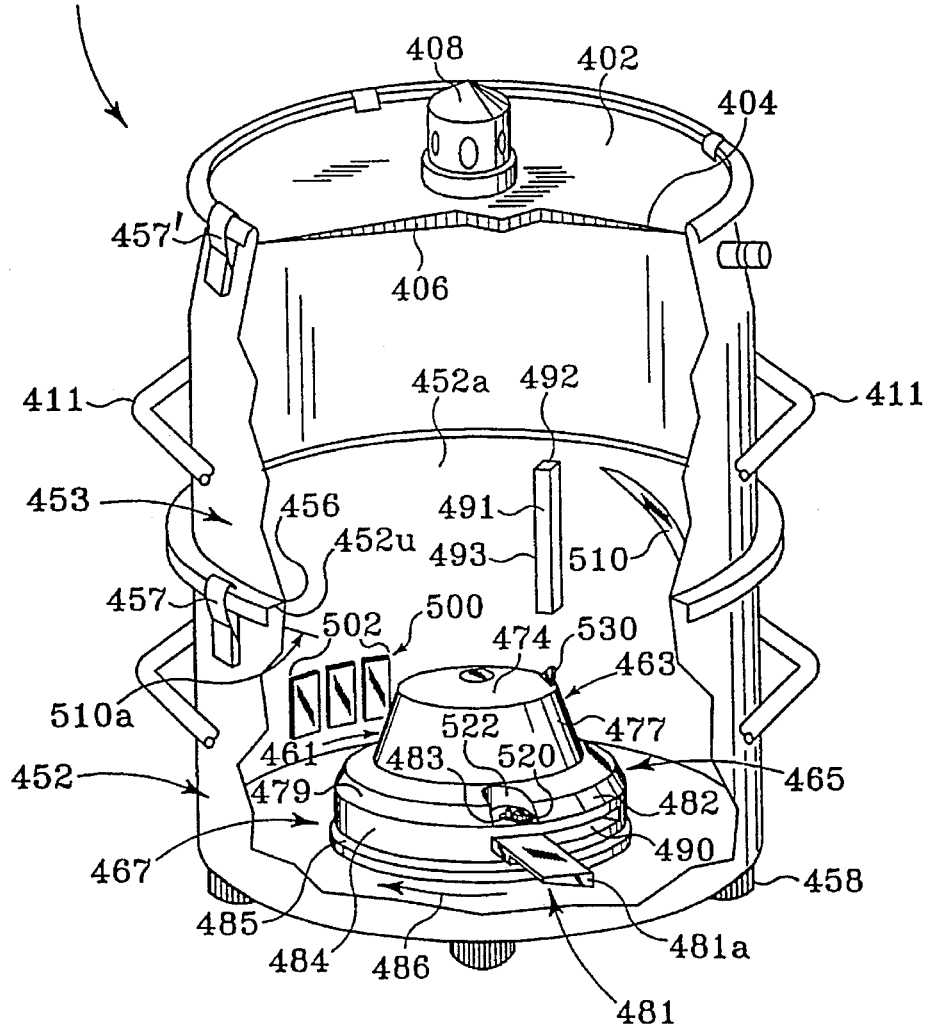
FIG. 14 is a perspective partially cut-away view of a further embodiment of a processing chamber provided by this invention.
Figure 15:
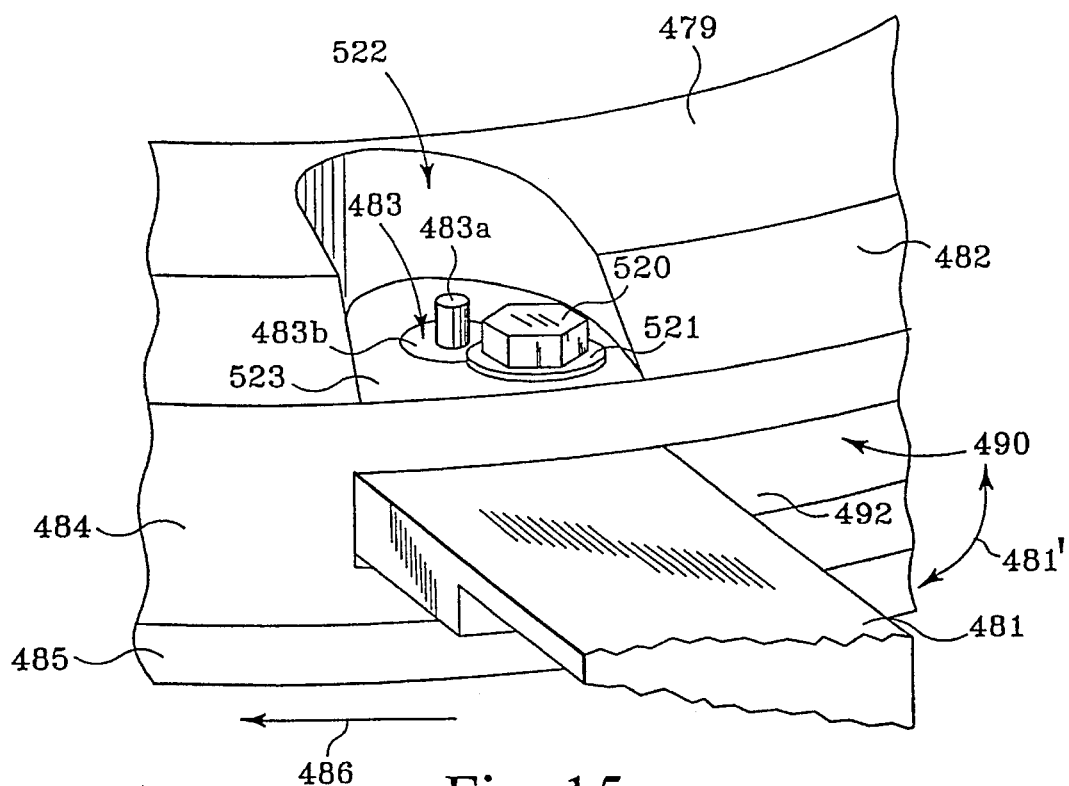
FIG. 15 is an enlarged partial perspective view of the means by which the cutting blades of the processing chamber of FIG. 14 are secured to the rotating hub assembly.
Figure 16:
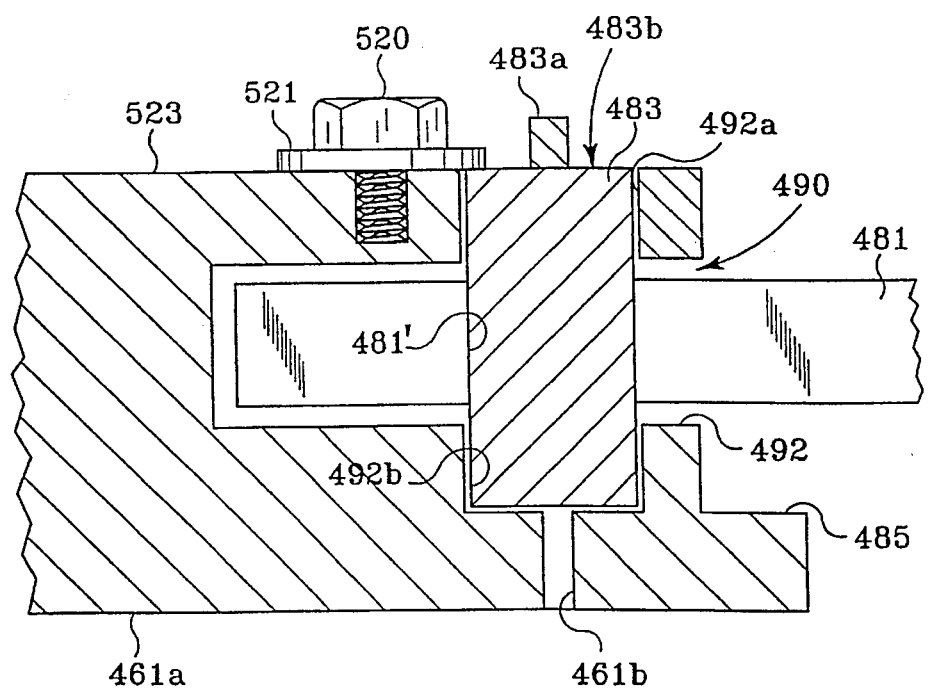
FIG. 16 is an enlarged partial cross section of the point of attachment of the pivoting cutting blades to the rotating hub assembly of FIG. 15.

Reference will now be made to FIGS. 14–16 which show an even further embodiment of a processing flask 451 and an impeller hub assembly 461 provided by this invention. The flask assembly 451 of this further embodiment includes a flask lower housing 452 and a flask top housing 453, which is arranged atop lower housing 452. The flask lower housing 452 has an outwardly turned upper circular flange 452U supporting the flask top housing 453 on a seal member (not shown), which seals against a circular bead at the bottom of the flask top housing 453. The top and lower housings are fastened together by over-center lever-operated spring clamps 457.

Figure 17:
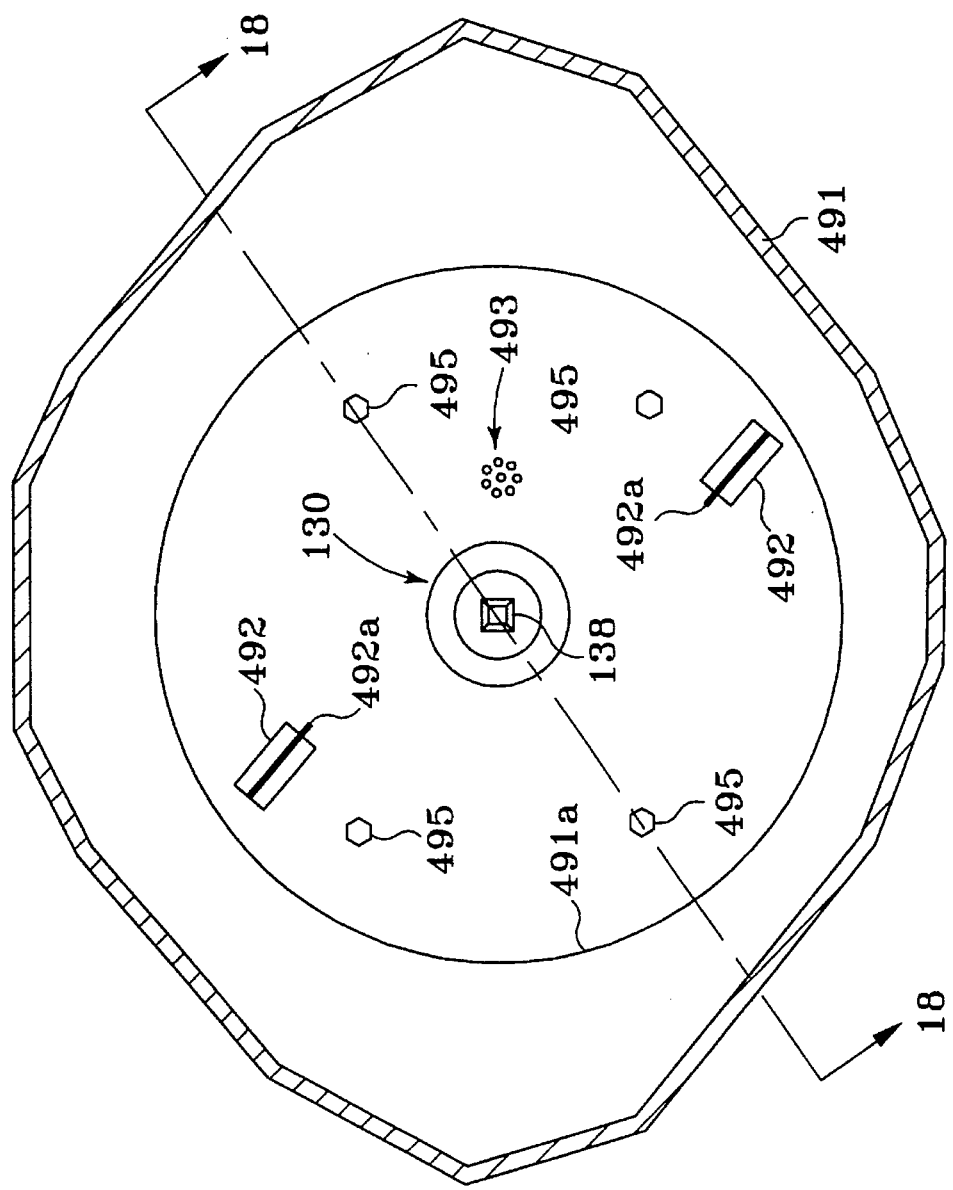
FIG. 17 is a top view of the inside of the cabinet of one embodiment of the invention to show the means to support and retain the waste processing flask and to handle any materials expelled from the waste processing flask during operation.
Figure 18:
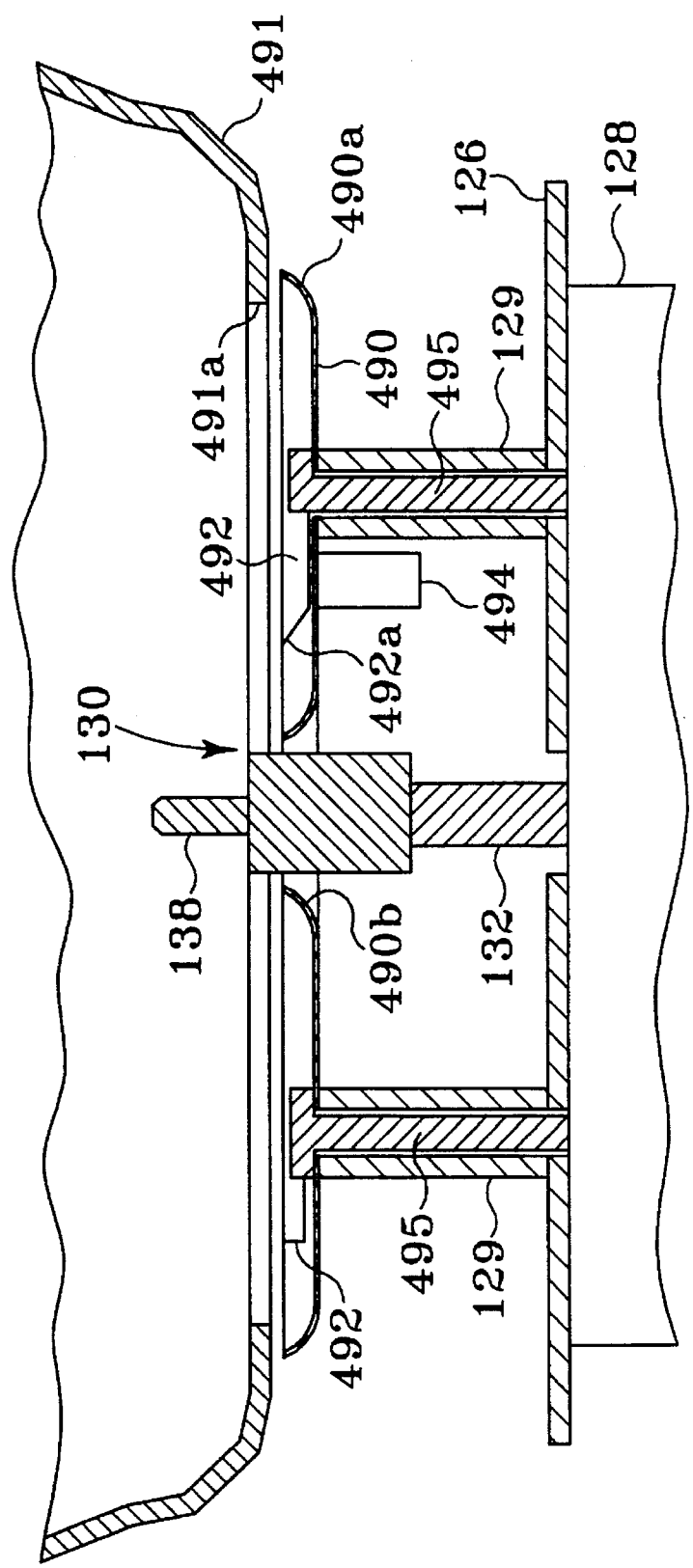
FIG. 18 is a partial cross-sectional view of FIG. 17.

Referring now to FIGS. 17 and 18, the bottom of the flask lower housing has four circularly spaced feet 458 (only three of which are shown in FIG. 14) which are received on an annular chamber base plate 490. These feet support the flask assembly 451 within the cabinet tub 491, and also prevent the flask assembly from rotating or climbing out under torque by pressing against stops 492 while operatively disposed within the cabinet tub. The annular chamber base plate 451 also features outer and inner liquid containment dams 490a and 490b, respectively, that retain spillage that may occur from the flask 451. The outer edge of the dam 490a extends beyond the opening in the cabinet tub 491a so that leakage into the cabinet tub 491 will fall into the chamber base plate 490. Liquids will drain through drainage tube inlet 493 into drainage tube 494 and be directed by a hose to a collection reservoir at the back of the cabinet.

The flask top housing 453 further includes a cap or top 402 positioned atop and fastened via clamps 457' to the top housing 453 enclosing its upper opening. A cap liner 404 is affixed to the underside of cap 402 to prevent waste material from clinging to the underside of cap 402. A plenum-like space 406 is formed between cap liner 402 and liner 404. Cap liner 402 is formed by a gas-permeable material that permits the flask 451 to breath through HEPA valve 408 in response to heated moist air through the entire cap liner 402.

A pair of T-type handles 411 can be provided on the side of the flask lower housing 452 for removal of the flask assembly 451 from the main cabinet by simply lifting the cabinet lid and lifting the flask assembly out of the cabinet by use of the T-handles, one in each hand. The flask assembly can be easily lifted off the coupler and moved to whatever site location is convenient for depositing medical waste material therein typically being generated.

An impeller hub assembly 461 is mounted in flask assembly 451 supported by a bearing mount cylinder assembly substantially similar to the manners in which hub assemblies 61, 161, 261, and 361 are mounted to their respective flask assemblies as described above. Accordingly, those details need not be repeated here.

Impeller hub assembly 461 is constructed in a substantially similar fashion to hub 261 shown and described in relation to FIGS. 11 and 12 and includes an upper portion 463, a middle portion 465 and a lower portion 467. Hub assembly 461 further includes a ring 485 disposed at the lowermost portion 467 to prevent soft medical waste from being carried under hub 461 while it rotates. Upper portion 463 preferably includes an inclined wall 477 and lower portion 467 preferably includes a cylindrical or vertical wall 484. An annular shoulder 479 is disposed normally to the rotation axis of hub 461 and an inclined frustoconical wall 482 is disposed in middle portion 465 interconnecting shoulder 479 and vertical wall 484. Two blades 481, driven in the direction (clockwise) of reference arrow 486, are mounted in recessed slots 490 formed in wall 484 and each is pivotally secured in place by a pin 483 and shoulder bolt 520, which are discussed in further detail below. Blades 481 are similarly shaped to blades 81, 181, 281 and 381 as described above and their shape can be better observed in FIGS. 4 and 5. As noted above, the blades of this invention are preferably made of a steel alloy, such as tool steel.

During treatment of medical waste in a rotating pulverizing apparatus such as provided by the invention, applicants have discovered that medical waste may be more effectively treated with a plurality of baffle means, each baffle means being located within the chamber and adapted for more effective treatment of differing medical waste. To more effectively treat the hard waste portion (e.g., medical sharps and the like) of the medical waste within the processing chamber, a first baffle means defined by an abutment bar 491 can be mounted on the inside upstanding cylindrical wall 452*a* of the flask lower housing 452 above the floor of the housing with its top 492 adjacent the top of the lower housing 452. Baffle bar 491 presents a 90° angle edge 493 facing the materials as they are driven around by impeller blades 481 moving in a clockwise direction (as shown by reference arrow 486). Baffle bar 491 is disposed in this embodiment higher above the rotating blades 481 than the arrangement of abutment bars 91, 191 shown and described in relation to FIGS. 2, 4 and 7. Baffle bar 491 is thus positioned to more effectively blunt and fractionalize the sharps and other non-soft waste traveling with the rotating mass within the chamber during operation. Baffle bar 491 stops rotation of the upper portion of the material within the chamber, allowing the material to fall into the path of the blades 481, enhancing the impact of blades 481 on the medical waste, and more effectively blunting and fractionalizing the non-soft waste.

As discussed and shown in relation to FIG. 5 above, the lower face of the blades 481 are inclined downwardly from the front or leading edge toward the rear or trailing edge. Consequently, the trailing edge of each blade is closer to the bottom floor of the flask lower housing than is the sharper leading edge as the blade rotates. This arrangement has a tendency to initially drive the waste materials downwardly. To more effectively treat the soft portion of the medical waste, a second baffle means 500, defined by one or more baffle bars, can be mounted on the inside upstanding cylindrical wall 452*a* of lower flask assembly 452 adjacent the bottom floor thereof. In a preferred embodiment, six (6) baffle bars 500 can be employed in two groups of three, diametrically opposed to one another in a plane lower than abutment bar 491. A radially inwardly extending deflector 510 is also mounted on the interior wall 452*a* for directing waste in a downwardly circulating motion into baffle bars 500 to facilitate its fractionalization and destruction. As shown in FIG. 14, deflector 510 is positioned to direct medical waste materials moving within the chamber to expose it particularly to the co-action of the baffle bars 500 and pivotal blades 481. Deflector 510 can be a ribbon of stainless steel having a thickness on the order of about 3/32 to about 3/16 of an inch and welded or otherwise fastened to the interior sidewall of the chamber in a downwardly extending direction from adjacent the upper portion of sidewall to adjacent the central portion of chamber sidewall 452. In preferred embodiments of the invention, the terminal portion 510*a* of deflector **510* is located "upstream" of the baffle bars 500 and their cutting edges 502 so that waste materials will, for example, leave the terminal portion 510*a* of deflector 510 with a high velocity directed at baffle bars 500, which provide a plurality of cutting edges at each of their respective corners 502 located only a small clearance distance from the ends 481*a* of the blades 481, as indicated in FIG. 14. The co-action of blade ends 481*a* and the cutting edges 502 of baffle bars 500 more effectively cut and tear soft medical waste material, such as those described above, into small pieces, while abutment bar 491 serves to more effectively fractionalize and dull non-soft medical waste of the type described above into a generally minced state.

The pair of blades 481 (only one blade is shown in FIG. 14) are pivotally mounted to the hub 461 at diametrically opposed locations of the hub 461 adjacent its lower portion 467 within recessed slots 490 provided in wall 484. As shown in FIGS. 15 and 16, each blade 481 is pivotally secured by an axle pin 483 that extends through a bore 492*a* through planar surface 523 and the adjacent portion of hub 461, and through a receiving hole 481' provided in blade 481 near its inner proximal end, and is received at its lower end in a bore 492*b* formed in the portion of hub 461 adjacent the lower surface 492 of slot 490. Axle pin 483 is secured in place by a shoulder bolt 520 received in a recessed cove area 522 formed in part by planar surface 523 provided in portions 479 and 482 of hub 461 as shown best in FIG. 15. Shoulder bolt 520 includes a skirt 521 that extends partially over an upwardly facing surface 483*b* of pin 483 to secure the pin within bore 492*a*. Shoulder bolt 520 is threadably fastened in a threaded bore 524 formed in surface 523 of cove 522. Bore 524 must be located sufficiently near pin-receiving bore 492 so that when pin 483 is in bore 492, the skirt 521 of shoulder bolt 520 extends partially over the top end 483*b* of pin 483. It is understood that other means of securing pin 483 in bore 492*a* may prove suitable and are therefore contemplated by this invention.

Axle pin 483 is preferably provided with a nipple 483*a* protruding upwardly above planar surface 523 of cove 522 when pin 483 is disposed within pin-receiving bore 492 to provide means for grasping pin 483 for removal. The portion of hub 461 adjacent its bottom underside surface 461*a* (FIG. 16) can further include means for dislodging pin 483 in the event one is unable to remove the pin 483 with nipple 483*a*.

Such means can include a bore 461b extending through hub 461 from the underside 461a and opening into pin-receiving bore 492b to allow one to use a punch and tap the pin 483 out of bore 492a from the underside. Pin 483 can also include a nipple (not shown) extending downwardly from its lower end and through or partially through bore 461b to facilitate the removal of pin 483 by tapping from the underside if desirable.

Axle pins 483 are preferably formed from hardened stainless steel to provide a more durable assembly. For example, blades 481 may be formed from steel with a hardness of Rc 60 for use with axle pin 483 formed from steel with a hardness of Rc 55.

Slots 490 are formed in the sidewall 484 of hub 461 and extend inwardly toward the center of hub 461. As with blades 281 and recessed slots 290 shown in FIGS. 11 and 12, each slot 490 includes a first forward impingement surface and a second rear impingement surface. When the hub 461 is rotating in the direction shown by reference arrow 486 (clockwise), the pivotal blades 481 are urged to pivot outwardly by centrifugal force to an extended position. The blades 481 are prevented from pivoting forwardly in the direction of rotation (arrow 486) substantially past a reference line extending radially outwardly from their pivotal mountings by the forward impingement surface of recessed slot 490. Upon contact with stationary or more slowly moving waste material, the blades 481 may pivot along reference path 481' to be partially received within slots 490, where the trailing edge of the blade impinges upon the second rear impingement surface of slot 490.

Hub 461 shown in FIG. 14 can further include a surface for breaking waste-carrying containers introduced into the waste treatment chamber comprising a spike or tooth-like member 530 equipped with a carbide metal tip and protruding upwardly and outwardly adjacent the outer edge of top surface 474 of the hub assembly 461. Spike 530 is effective in disintegrating waste-carrying containers made of polystyrene or other friable material such as container 201 described above (see FIG. 8).

The apparatus of this invention includes hub-mounting features permitting the rotating hubs to be interchanged with little effort. As noted, hub assemblies 261, 361 and 461 shown in FIGS. 11-16, respectively, can all be interchangeably mounted and employed in the waste treatment apparatus of this invention described above and shown in FIGS. 2, 7 and 14. More particularly, as with the apparatus shown in FIG. 2, the apparatus of FIGS. 7-16 includes a lower ball bearing assembly (166) and an upper ball bearing assembly (167) spaced several inches apart, and supported by, a bearing supporting cylinder (162), which is welded to the bottom of the flask assembly. The inner race of bearings (166) and (167) carry the impeller shaft (168). This assembly provides a rugged and durable rotatable support of the rotating waste destruction and treatment assembly (which includes pivotal blades 81, 181, 281, and 481, and rotating fenders and surfaces 211, 211b and 300), which must endure intense shock loads during operation. The combination of the pivotable blades, which are pivotally mounted intermediate the upper and lower bearings, and the spaced ball bearing support provided by the impeller shaft provide a waste treatment assembly which can endure the torturous abuse imposed by the combined effects of solid and/or soft medical waste being processed.

Referring now to FIG. 9, the motor 128 is securely mounted at its upper end to a support plate 126 which is carried by a plurality of vibration isolator couplings 124 to the frame 122 which is vibrationally isolated from the walled enclosure 310. As shown in FIGS. 17 and 18, chamber base plate 490 is carried above support plate 126 by a plurality of tubular spacers 129 and fastened in place by a plurality of bolts 495. As indicated above the chamber base plate 490 includes a pair of stops 492 which are fastened to the upper surface of the chamber base plate 490 to engage the feet 458 of the flask 451. The stops 492 preferably each have a projecting pointed corner 492a which will sink into the elastomeric feet 458 of the flask and, in addition to preventing its rotation, will provide force holding the flask 451 against the chamber base plate 490. Annular chamber base plate 490 has a central opening 130 which permits a driving coupling 138 from the rotating shaft 132 of the driving motor to extend into the keyed opening of the impeller shaft of the particular rotating hub assembly employed with the system. Thus, the entire rotational waste treatment assembly and its driving motor are suspended within the walled enclosure and openable top (FIG. 1) by a vibration isolating structure. There is no mechanical connection between the sidewalls 143 of the centralized tub portion 142 of the enclosure and the annular chamber base plate 490 or any other portion of the waste treatment operating apparatus. The opening 492 in the central portion of the apparatus enclosure 491 overlaps the outside dimension of the chamber base plate 490, but is separated by a gap, as shown in FIG. 18, so that the chamber base plate 490 may move with the motor and chamber freely while not contacting the central portion of the housing 491, so as not to transmit vibration from the isolated portion of the apparatus to the stationary portion of the apparatus.

Thus, in the apparatus of the invention shown in FIGS. 7-16, vibration and sound are trapped and deadened in an improved manner within the enclosure for the apparatus, and the operating portion of the waste treatment apparatus including the flask assembly, driving motor and the intervening supporting structure, are isolated from the enclosure by elastomeric sound and vibration deadening elements. The driving motor and waste destruction chamber are thus isolated from the apparatus housing.

Where the description above refers to used hypodermic needles, it should be recognized that not only the metal needle portion but the entire syringe assembly may be safely collected and processed by this invention. In addition, disposable scalpels and other sharp solid medical waste and even soft medical waste may also be collected and safely disposed of. Following the collection of solid medical waste in a medical waste container, the entire container may be carried to and inserted in the waste treatment chamber for treatment as shown and described above.

While the invention has been illustrated and described in detail in the drawings and foregoing description, the same is to be considered as illustrative and not restrictive in character, it is to be understood that only preferred embodiments have been shown and described and that all changes and modifications that come within the spirit of the invention are desired to be protected.

What is claimed is:

1. A medical waste treatment apparatus, comprising:

portable means forming a closeable chamber adapted to be coupled with a motor, said chamber having an imperforate and generally cylindrical sidewall and a closed bottom floor and being adapted to receive and treat solid and soft medical waste;

a rotatable assembly carried within said chamber adapted to be rotatably driven by said motor;

first means carried by said rotatable assembly for moving and treating medical waste during rotation of said rotatable assembly;

first baffle means fixedly disposed on the interior sidewall of said chamber at a height above the bottom floor for acting upon a first portion of the medical waste as said medical waste is moved within said chamber during operation; and second baffle means fixedly disposed on the interior sidewall of said chamber generally at a height generally lower than the height of said first baffle means for acting upon a second portion of the medical waste as said medical waste is moved within said chamber during operation, whereby said first and second baffle means cooperate with the first means to enhance the treatment of said medical waste.

2. The medical waste treatment apparatus of claim 1 wherein said first baffle means is located for impact by non-soft materials.

3. The medical waste treatment apparatus of claim 1 wherein said second baffle means is located for tearing of soft and fibrous materials.

4. The apparatus of claim 1 further comprising second means carried by said rotatable assembly for preventing soft medical waste from being urged under said rotatable assembly during operation.

5. The apparatus of claim 4 wherein said second means comprises a ring extending radially outwardly from adjacent the lowest portion of said rotatable assembly.

6. The apparatus of claim 1 further comprising third means carried by said rotatable assembly for impacting and fractionalizing a container formed of imperforable material for collection of said medical waste outside of the medical waste treatment chamber.

7. The apparatus of claim 6 wherein said third means comprises a hard protrusion extending upwardly and outwardly from adjacent the top portion of said rotatable assembly.

8. The medical waste treatment apparatus of claim 1 further comprising a separate unit providing power for rotation of the rotatable assembly and an enclosure for said chamber-forming means during operation of the rotatable assembly, and means, within said enclosure, for supporting and retaining said chamber-forming means and for collecting leakage from said chamber-forming means during operation.

9. The medical waste treatment apparatus of claim 8 wherein said means includes a supporting plate having liquid containment dams for retention of leakage.

10. The medical waste treatment apparatus of claim 9 wherein said supporting plate includes a plurality of stops for engaging (said closeable chamber) and preventing its rotation during operation.

11. The medical waste treatment apparatus of claim 9 wherein said supporting plate is a concave annulus with said containment dams formed by its inner and outer edges.

12. A medical waste treatment apparatus, comprising:

means forming a chamber adapted to be coupled with a motor, said chamber having a generally cylindrical sidewall and a bottom floor and being adapted to receive and treat solid and soft medical waste;

a rotatable assembly carried within said chamber adapted to be rotatably driven by said motor;

first means carried by said rotatable assembly for moving and treating medical waste during rotation of said rotatable assembly, the first means comprising a plurality of waste treating blades pivotally mounted on a rotatable hub to rotate within said closeable chamber adjacent its bottom, each of said plurality of waste treating blades having an opening formed therein adjacent one end disposed in axial alignment with a corresponding bore formed in said rotatable hub and being pivotable between a first position where the blade extends substantially radially outwardly from its mounting and a second position where the blade is partially recessed within said rotatable hub, and a threadless axle pin extending through each said hub bore and each said blade opening to rotatably secure each said blade within said slot, said threadless axle pin being retained within each said bore formed in said rotatable hub by retaining means carried by said rotatable hub;

first baffle means fixedly disposed on the interior sidewall of said chamber at a height above the bottom floor for acting upon a first portion of the medical waste as said medical waste is moved within said chamber during operation; and second baffle means fixedly disposed on the interior sidewall of said chamber generally at a height lower than the height of said first baffle means for acting upon a second portion of the medical waste as said medical waste is moved within said chamber during operation, whereby said first and second baffle means cooperate with the first means to enhance the treatment of said medical waste.

13. The apparatus of claim 12 wherein said rotatable hub includes a substantially horizontal surface portion formed about each said bore and said means for securing each said threadless axle pin within each said bore comprises a fastener threadably connected to the rotatable hub at the substantially horizontal surface portion, and wherein each said threadless axle pin includes a substantially planar upper surface, and said fastener provides a substantially planar surface for engagement with the substantially planar surface of said threadless axle pin.

14. The apparatus of claim 13 wherein each said threadless axle pin comprises an annular upper surface and each means for retaining each said threadless axle pin within each said bore comprises a screw fastener with a skirt portion for engagement with the annular upper surface of said threadless axle pin, said threadless axle pin being free to rotate in said bore.

15. The apparatus of claim 14 wherein each of said threadless axle pins is retained within each said bore by a shoulder bolt.

16. The apparatus of claim 14 wherein the threadless axle pin includes a upwardly extending nipple within the upper surface.

17. Apparatus for the treatment of medical waste, comprising:

a portable housing forming a chamber defined by a bottom, sidewall and top and a closeable chamber opening in the top permitting insertion of medical waste into said chamber;

a rotatable hub carried by the chamber bottom and at least one blade pivotally carried by said rotatable hub, said hub including at least one blade-receiving slot formed therein in which said at least one blade is mounted, said at least one blade being pivotable between a first extended position where said blade extends substantially radially outwardly from its mounting and a second retracted position where the blade is partially recessed within said hub, each of said waste treating blades having an opening formed therein adjacent their proximal ends disposed in axial alignment with a corresponding bore formed in said hub, said rotatable hub further comprising a rotatable axle pin extending downwardly through said bore in said hub and said blade opening to pivotally secure said blade within said slot, said rotatable hub further comprising means for securing said axle pin within the bore formed in said hub, said rotatable hub further comprising an annular ring extending outwardly from said rotatable hub from below said at least one blade-receiving slot;

abutment means formed on the chamber sidewall comprising first abutment means and second abutment means, said second abutment means being disposed on the chamber sidewall at a location lower than that of said first abutment means and providing at least one cutting edge only a small clearance distance from the distal ends of said waste treating blades; and a separate power unit including a motor to drive the rotatable hub of said portable housing.

18. The apparatus of claim 17 further comprising means for directing medical waste materials moving within the chamber to expose it to the combined action of the second abutment means and said waste treating blades.

19. The apparatus of claim 18 wherein said waste-directing means includes one or more deflectors extending radially inwardly from the chamber sidewall and extending angularly downwardly from adjacent an upper portion of said chamber sidewall to adjacent a central portion thereof, each said deflector having a terminal portion disposed upstream of and adjacent to said second abutment means so that waste material leaving the terminal portion of said deflector will be directed at said second abutment means to facilitate the processing and pulverizing of said waste material.

20. The apparatus of claim 17 wherein said at least one blade-receiving slot forms a first surface impeding the pivoting of the adjacent blade forwardly in the direction of rotation of said hub substantially past a reference line extending radially outwardly from its pivotable mounting.

21. The apparatus of claim 20 wherein said at least one blade-receiving slot further forms a second surface impeding the pivoting of the adjacent blade rearwardly so that while in its retracted position, said blade is partially recessed within said hub.

22. The apparatus of claim 17 wherein said closeable chamber opening is sufficiently large to receive a breakable container for medical waste, and said rotatable hub further comprises a container-breaking surface for disintegrating said breakable container and for exposing the contained medical waste and container fragments to treatment within said chamber.

23. A medical waste treatment apparatus, comprising:

means forming a chamber adapted to be coupled with a motor, said chamber having a generally cylindrical sidewall and a bottom floor and being adapted to receive and treat solid and soft medical waste;

a rotatable assembly carried within said chamber adapted to be rotatably driven by said motor;

first means carried by said rotatable assembly for moving and treating medical waste during rotation of said rotatable assembly, wherein said first means comprises at least one metal blade pivotally affixed to said hub member in a slot formed in said rotatable assembly, said slot having a first stop surface for impeding the blade from pivoting forwardly substantially past a reference line extending radially outwardly from its mounting and having a second surface for impeding the blade from pivoting rearwardly substantially past about 90° from said reference line, wherein said rotatable assembly further comprises a ring extending radially outwardly from adjacent its lowest portion, wherein said rotatable assembly further comprises a hard protrusion extending upwardly and outwardly from adjacent its top portion;

first baffle means fixedly disposed on the interior sidewall of said chamber at a height above the bottom floor for acting upon a first portion of the medical waste as said medical waste is moved within said chamber during operation, wherein said first baffle means comprises at least one baffle for providing surfaces located for preferential action on non-soft medical waste material during operation, and second baffle means fixedly disposed on the interior sidewall of said chamber generally at a height lower than the height of said first baffle means for acting upon a second portion of the medical waste as said medical waste is moved within said chamber during operation, whereby said first and second baffle means cooperate with the first means to enhance the treatment of said medical waste, wherein said second baffle means comprises a plurality of baffles for providing surfaces located for preferential action on soft medical waste material during operation.

24. A medical waste treatment apparatus, comprising:

means forming a chamber adapted to be coupled with a motor, said chamber having a generally cylindrical sidewall and a bottom floor and being adapted to receive and treat solid and soft medical waste;

a rotatable assembly carried within said chamber adapted to be rotatably driven by said motor;

first means carried by said rotatable assembly for moving and treating medical waste during rotation of said rotatable assembly;

first baffle means fixedly disposed on the interior sidewall of said chamber at a height above the bottom floor for acting Upon a first portion of the medical waste as said medical waste is moved within said chamber during operation;

second baffle means fixedly disposed on the interior sidewall of said chamber generally at a height generally lower than the height of said first baffle means for acting upon a second portion of the medical waste as said medical waste is moved within said chamber during operation, whereby said first and second baffle means cooperate with the first means to enhance the treatment of said medical waste;

an enclosure for said chamber during operation of the waste treatment apparatus; and a supporting plate supported free of contact with said enclosure, said supporting plate having a liquid containment dam for retention of leakage.

25. A medical waste treatment apparatus, comprising:

means forming a chamber adapted to be coupled with a motor, said chamber having a generally cylindrical sidewall and a bottom floor and being adapted to receive and treat solid and soft medical waste said chamber having a plurality of elastomeric feet for supporting the chamber, a rotatable assembly carried within said chamber adapted to be rotatably driven by said motor;

first means carried by said rotatable assembly for moving and treating medical waste during rotation of said rotatable assembly;

first baffle means fixedly disposed on the interior sidewall of said chamber at a height above the bottom floor for acting upon a first portion of the medical waste as said medical waste is moved within said chamber during operation;

second baffle means fixedly disposed on the interior sidewall of said chamber generally at a height generally lower than the height of said first baffle means for acting upon a second portion of the medical waste as said medical waste is moved within said chamber during operation, whereby said first and second baffle means cooperate with the first means to enhance the treatment of said medical waste;

an enclosure for said chamber during operation of the waste treatment apparatus; and a supporting plate supported free of contact with said enclosure, said supporting plate having a liquid containment dam for retention of leakage and a plurality of stops having projecting corners for deformation and engagement of the elastomeric feet for preventing rotation of the chamber during operation of the waste treatment apparatus.

26. The medical waste treatment apparatus of claim 25 wherein said projecting corners impose a downward force on said elastomeric feet during operation.

27. A medical waste treatment apparatus, comprising:

a portable medical waste treatment chamber formed by an imperforate and generally cylindrical sidewall and a closed bottom floor, said portable medical waste treatment chamber being adapted to receive and treat solid and soft medical waste and to be coupled with a separate motor;

a rotatable assembly carried within said portable chamber with a shaft extending through the bottom floor adapted to be rotatably driven by said motor;

said rotatable assembly carrying a plurality of pivotable blades for moving and treating medical waste during rotation of said rotatable assembly;

first baffle means fixedly disposed on the interior sidewall of said chamber at a height above the bottom floor and said pivotable blades for acting upon a first portion of the medical waste as said medical waste is moved within said chamber during operation, second baffle means fixedly disposed on the interior sidewall of said chamber at a height generally lower than the height of said first baffle means and adjacent said pivotable blades for acting upon a second portion of the medical waste as said medical waste is moved within said chamber during operation, whereby said first and second baffle means cooperate with the rotatable assembly to enhance the treatment of said medical waste.

28. The medical waste treatment apparatus of claim 27 wherein said rotatable assembly further comprises a ring extending radially outwardly below said pivotal blades.

* * * * *